United States Patent [19]
Liang

[11] Patent Number: 5,953,448
[45] Date of Patent: Sep. 14, 1999

[54] CONTOUR MEASUREMENT OF AN OBJECT HAVING A DISCONTINUOUS SURFACE USING BLOCK POINT IDENTIFICATION TECHNIQUES

[75] Inventor: Wei-Shi Liang, Cary, N.C.

[73] Assignee: Textile/Clothing Technology Corporation, Cary, N.C.

[21] Appl. No.: 08/609,538

[22] Filed: Mar. 1, 1996

[51] Int. Cl.$^6$ .............................. G06K 9/00; G06K 9/46; G06K 9/48; G01B 11/24

[52] U.S. Cl. .......................... 382/154; 382/190; 382/199; 356/376

[58] Field of Search .................................... 382/108, 141, 382/197, 199, 300, 203, 205; 356/376, 359, 377, 381; 250/237, 559.22; 395/141; 358/448, 455, 456, 466

[56] References Cited

U.S. PATENT DOCUMENTS

| | | | |
|---|---|---|---|
| 4,188,124 | 2/1980 | Jaerisch et al. | 356/356 |
| 4,298,283 | 11/1981 | Makosch et al. | 356/351 |
| 4,641,972 | 2/1987 | Holioua et al. | 356/376 |

OTHER PUBLICATIONS

Bieman, et al.; Absolute Measurement Using Field Shifted Moire; *SPIE–The International Society for Optical Engineering;* vol. 1614; (1991); pp. 259–264 Nov. 14–15, 1991.

Boehnlein, et al.; Field Shift Moire, A New Technique For Absolute Range Measurement; *SPIE–The International Society for Optical Engineering;* vol. 1163; (1989); pp. 2–13.

Srinivasan, et al.; Automated Phase–Measuring Profilometry: A Phase Mapping Approach; *Applied Optics;* vol. 24, No. 2; (Jan. 15, 1985); pp. 185–188.

Wyant; Use of an AC Heterodyne Lateral Shear Interferometer With Real–Time Wavefront Correction Systems: *Applied Optics;* vol. 14, No. 11; (Nov. 1975); pp. 2622–2626.

Bruning, et al.; Digital Wavefront Measuring Interferometer for Testing Optical Surfaces and Lenses; *Applied Optics;* vol. 13, No. 11; (Nov. 1974); pp. 2693–2703.

Chang et al.; Phase–measuring Profilometry Using Sinusoidal Grating; *Experimental Mechanics;* pp. 117–122 (Jun. 1993).

Halioua et al.; Optical Sensing Techniques for 3–D Machine Vision; *SPIE–The International Society for Optical Engineering;* vol. 665; pp. 150–161 (1986).

Indebetouw; Profile Measurement Using Projection of Running Fringes; *Applied Optics;* vol. 17, No. 18; pp. 2930–2933; (Sep. 15, 1978).

Reid et al.; Moire Topography With Large Contour Intervals; *SPIE–The International Society for Optical Engineering;* vol. 814; pp. 307–313 (1987).

Su et al.; Phase–stepping Grating Profilometry: Utilization of Intensity Modulation Analysis in Complex Objects Evaluation; *Optics Communications;* vol. 98, No. 1, 2, 3; pp. 141–150; (Apr. 15, 1993).

(List continued on next page.)

*Primary Examiner*—Jose L. Couso
*Assistant Examiner*—Duy M. Dang
*Attorney, Agent, or Firm*—Myers Bigel Sibley & Sajovec, P.A.

[57] ABSTRACT

Systems, methods, and apparatus for enabling the use of phase measurement profilometry techniques for measuring the surface contour of an object having a surface discontinuity thereon are disclosed. A method for correcting optical phase orders in a computer-generated image includes selecting a local region and linking identified key data points and block points with a blocking line. An intensity value of zero is assigned to each pixel located on the blocking line from which the correct optical phase order for each pixel in the local region can then be determined. Multiple block point identification methods are provided, the particular combination of which is highly efficient in locating block points in an area adjacent a surface discontinuity.

17 Claims, 18 Drawing Sheets

OTHER PUBLICATIONS

Baxes; Digital Image Processing: A Practical Primer—Chapter 6—Image Data Handling; Cascade Press, Denver, Colorado; pp. 69–106 (1984).

Baxes; Digital Image Processing; A Practical Primer—Chapter 7—Image Data Processor; Cascade Press, Denver, Colorado; pp. 107–126; (1984).

Baxes; Digital Image Processing; A Practical Primer—Chapter 5—Picture Operations; Cascade Press, Denver, Colorado; pp. 51–56; (1984).

BRIGHT SHADED

5,953,448

CONTOUR MEASUREMENT OF AN OBJECT HAVING A DISCONTINUOUS SURFACE USING BLOCK POINT IDENTIFICATION TECHNIQUES

FIELD OF THE INVENTION

This invention relates generally to surface profilometry, and more specifically to calculating the surface contour of objects having discontinuities in the surface thereof.

BACKGROUND OF THE INVENTION

The surface height, or contour, of a three-dimensional (3-D) object can be determined quickly and easily by various non-contact optical methods such as moire topography, Fourier transform profilometry, spatial phase detection, and phase measuring profilometry (PMP). There are a wide range of practical applications to which these profilometric measurement methods can be directed, such as topographical mapping and measurement of the human body.

In a PMP system, light having a sinusoidal intensity distribution is projected onto a 3-D object to produce optical fringes. The pattern of fringes, as seen by a remotely positioned camera, can be represented mathematically as a function of the intensity distribution. By comparing the intensity distribution of the light patterns on the 3-D object, distorted by the contour of the object, with the intensity distribution of the same pattern of light projected onto a known reference plane, it is possible to compute, using basic geometry and multiple phase shifts, the surface height of each point on the 3-D object, relative to the reference plane. By computing the height of each point on the object, the surface contour of the object can be accurately measured.

The PMP method of surface height measurement works well for objects having generally continuous surfaces. However, when a pattern of light is projected onto an object having surface discontinuities, such as where one portion of the object overlaps another portion, several problems arise. First, some of the pixels of the captured image in these regions may not have reliable optical phase orders. Second, the phase order of neighboring pixels may vary by more than one. This is often referred to as "jump order."

Because of these problems, the measurement of surface contour in regions adjacent such a discontinuity is difficult using the PMP method, thus limiting the practical applications of the PMP method. For example, when a pattern of light is projected onto a human body that is turned at a slight angle from center, various discontinuities and shadowy regions appear in areas between the chest and arms, and between the legs. A camera typically is unable to distinguish the break point between an arm and the chest, based on the fringe pattern observed. As a result, the determination of surface contour at these locations is difficult, often times resulting in an incomplete measurement of the body contour.

Various solutions have been proposed to overcome the problems presented by surface discontinuities when performing surface contour measurement techniques. Reid et al. describe a modified version of Moire topography in which the contour interval has been greatly increased so that the entire depth of an object lies within one fringe. (See, G. T. Reid et al., *Moire Topography With Large Contour Intervals*, SPIE Vol. 814, Photomechanics and Speckle Metrology, p. 307–313, 1987). Unfortunately, this method is complicated and may not return highly accurate data around discontinuities.

Su et al. describe a method for phase-stepping grating profilometry of complex objects wherein both the discrete phase distribution and the modulation depth distribution are calculated. (See, X. Su et al., *Phase-stepping Grating Profilometry: Utilization of Intensity Modulation Analysis in Complex Objects Evaluation*, Optics Communications, Vol. 98, p. 141–150, 1993). Blocking lines are constructed by tracing down local minima in modulation depth function values and linking the pairs of poles having opposite signs. The blocking lines generally follow the lines of physical discontinuities. Unfortunately, these blocking lines may be difficult to generate automatically by a computer analyzing the digital image. This method also is complicated because the use of a mask may be required which may not return highly accurate data around discontinuities.

SUMMARY OF THE INVENTION

It is therefore an object of the present invention to facilitate using PMP techniques for accurately measuring the surface contour of an object having surface discontinuities thereon.

It is yet another object of the present invention to facilitate the correction of optical phase orders for pixels comprising an image of an object having a surface discontinuity thereon.

These and other objects are accomplished according to the present invention, by systems, methods, and apparatus that facilitate measuring the surface contour of an object having a surface discontinuity thereon. According to the present invention, optical phase orders of pixels in a computer-generated image are determined. The image represents an object with a surface discontinuity and having a light beam with sinusoidally varying intensity projected thereon. A local region of the image surrounding the discontinuity is selected, and a key data point and block points within the local region are identified.

A key data point is defined to be a point that is easily located and that is generally the point where one portion of an object overlaps another portion. For example, the intersection point of the contour curve of an arm that appears to overlap the torso in an image of the human body, is a key data point. Key data points are significant in that they facilitate locating block points within a local region of a computer-generated image. A block point is defined to be a break point in the edge that appears in a computer-generated image where one portion of an object overlaps another portion.

The identified key data point and block points are linked with a blocking line. Linking key data points and block points with a blocking line facilitates separating the overlapping portion from the overlapped portion of an object in a computer-generated image. For example, a blocking line is the edge between the arm and chest (or between two legs) when one appears to overlap the other in a computer-generated image. The blocking line separates the arm and the chest in the image.

An intensity value of zero is assigned to each pixel located on the blocking line. The correct optical phase order for each pixel in the local region is then determined. First a method of assigning phase orders will check each pixel with a threshold to determine if the pixel belongs to the object in the image, or if it is part of the background. Background pixels have an intensity value of zero or less than a threshold. The method of assigning phase orders can determine the order of a pixel from an adjacent pixel that has an assigned order. The phase order assignment method will assign an order to each pixel of an image of the surface of an object beginning on one side of the object and continuing to the other side as described in U.S. Pat. No. 4,641,972 to Halioua et al. PMP techniques cannot determine the order of a pixel from a pixel across a background point. Therefore, the blocking line can avoid phase order assignment between pixels on opposite sides of an apparent discontinuity.

According to the present invention, block points are identified by performing multiple series of calculations using the optical phase order of each of the pixels within a selected local region. In the first series of calculations, the direction of block point search is the same as the direction of order assignment. It is determined whether the value of the optical phase order of a first pixel minus the value of the optical phase order of an adjacent second pixel on the same row and previous column of the array as the first pixel is less than zero. If this is true, the first pixel is designated as a block point and stored. If this is not true, it is then determined whether the value of the optical phase order of the first pixel minus the value of the optical phase order of the adjacent second pixel on the same row and previous column of the array as the first pixel is greater than one. If this is true, the first pixel is designated as a block point and stored. If this is not true, it is then determined whether the value of the optical phase order of the first pixel minus the value of the optical phase order of the adjacent second pixel, on the same row and previous column of the array as the first pixel, is equal to one, and it is then determined whether the value of the optical phase order of a third pixel, adjacent the first pixel on the same row and next column of the array as the first pixel, minus the value of the optical phase order of the first pixel is equal to one. If this is true, the first pixel is designated as a block point and stored. If this is not true, it is then determined whether the absolute value of the optical phase order of the first pixel minus the optical phase order of a fourth pixel adjacent the first pixel on the same column of the array as the first pixel, is equal to one, and it is determined whether the absolute value of the optical phase order of the second pixel, adjacent the first pixel on the same row of the array as the first pixel, minus the optical phase order of a fifth pixel, adjacent the second pixel on the same column of the array as the second pixel and adjacent the fourth pixel on the same row of the array as the fourth pixel, is equal to one. If this is true, the first pixel is designated as a block point and stored. If this is not true, the process proceeds to the next pixel in the local region and performs the above steps. The method proceeds systematically through the local region, and the above steps are repeated for each pixel.

The next series of calculations comprises determining whether the absolute value of the difference in intensity between a pair of adjacent pixels located on adjacent rows of the local region is greater than a threshold value. Each one of the pixels has a local maximum or local minimum (relative extremum) intensity value on the row. One fringe with relative extremum (local maximum or minimum) intensity value (peak or valley) should be continuous on a continuous surface. But the fringe may be broken in the discontinuous part. Typically, the threshold intensity value is about 50 grade value.

The final series of calculations comprise general imaging edge detection methods based on the average intensity image of four frames of each view. For each view, images with sinusoidal intensity distribution will be taken with four phase shifts in PMP. The fringes are shifted one quarter (¼) of a period each time. The images are stored in four (4) frame buffers of the image device. The average intensity image can be obtained by adding the intensity values of the corresponding pixel with same coordinates in the four image frame buffers and then dividing by four (4). Edge detection subroutines of the image processing library are then used in the local region. The points of edge detected are block points.

The combination of block point identification techniques set forth by the present invention, is highly efficient in locating block points. Using only traditional edge enhancement techniques, it typically has not been possible to successfully locate all existing block points in an area having a discontinuity. Consequently, the present invention enables a blocking line to be generated with greater accuracy, thereby facilitating the assignment of the correct optical phases to each pixel adjacent a discontinuity.

The present invention embodied in a computing environment may be used to determine the surface contour of an object having a surface discontinuity thereon. The computing environment includes a detector for receiving an image of the object, a display for displaying, via an array of pixels, the image of the object, and storage capability for storing optical phase and intensity values for each pixel in the array. In particular, a beam of light, having a sinusoidally varying intensity pattern, is projected onto an object. A deformed grating image of the object is received and stored for a plurality of phase shifts of the beam of light. For points on the surface of the object represented by a pixel, the height at each point, with respect to a reference plane, is then determined. Next, key data points are identified, then a local region of the received image, comprising pixels surrounding the discontinuity, is selected by reference to key data point. Block points are then identified within the local region, as described above. The key data point and the identified block points are linked with a blocking line, and an intensity value of zero is assigned to each pixel located on the blocking line.

Next, the optical phase order for each pixel in the local region is determined, as described previously. Utilizing the correct phase orders for the pixels in the local region, the height at each point with respect to a reference plane can be determined for each point on the surface of the object represented by a pixel. Consequently, the surface contour can be accurately determined for the object, even in an area having a discontinuity.

DETAILED DESCRIPTION OF PREFERRED EMBODIMENTS

Figure 1:
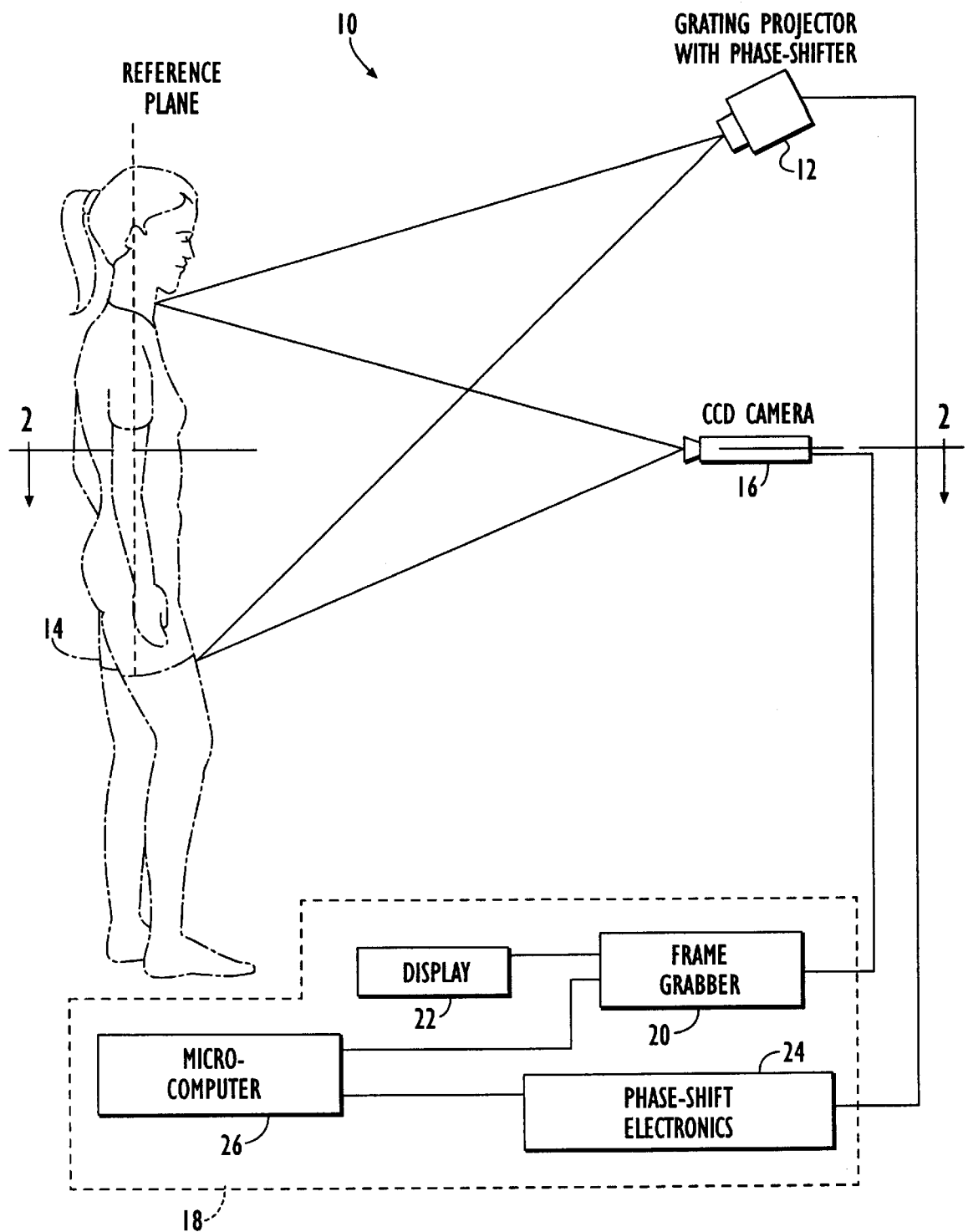
FIG. 1 illustrates a system for determining the surface contour of an object, such as the human body, having surface discontinuities thereon, according to the present invention.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, the thickness of layers and regions may be exaggerated for clarity. Like numbers refer to like elements throughout.

Referring now to FIG. 1, a system for determining the surface contour of a three-dimensional (3-D) object having surface discontinuities thereon is schematically illustrated. The system 10 comprises a light projector 12 for projecting a pattern of light having sinusoidally varying intensity onto a 3-D object 14, the image of which is captured by a plurality of charged couple device (CCD) cameras 16, and then processed and stored by an image processing system 18.

The light is preferably a conventional slide projector, modified to operate with a grating slide through which light is projected to produce a pattern having a sinusoidally varying intensity. However, as would be known by those having skill in the art, other means for projecting light having phase shift capability can be used. For example, a sinusoidal light pattern can be projected onto the surface of a 3-D object by generating an interference pattern between two coherent plane wavefronts via a Twyman-Green interferometer using a single-frequency laser source.

The slide is preferably mounted on a stepper motor-driven translation stage to permit the phase of the sinusoidal light pattern to be shifted by a predetermined amount. As is known to those having skill in the art of PMP techniques, shifting the phase of the sinusoidal pattern of light allows the slope of a 3-D object 14 to be determined, thereby allowing concave portions to be distinguished from convex portions of the surface.

Figure 3A:
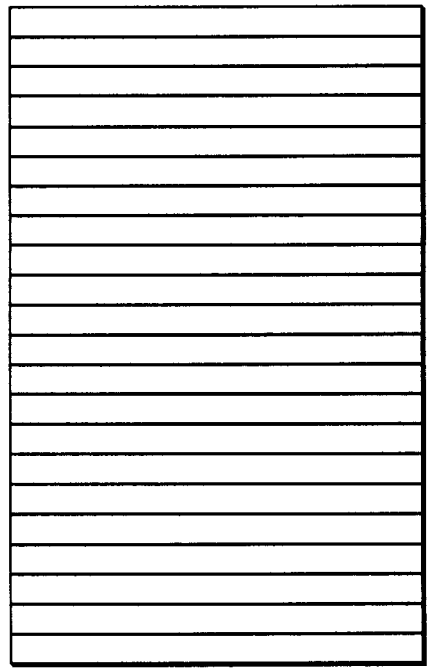
FIG. 3A illustrates a pattern of light having sinusoidally varying intensity projected onto a flat reference plane.
Figure 3B:
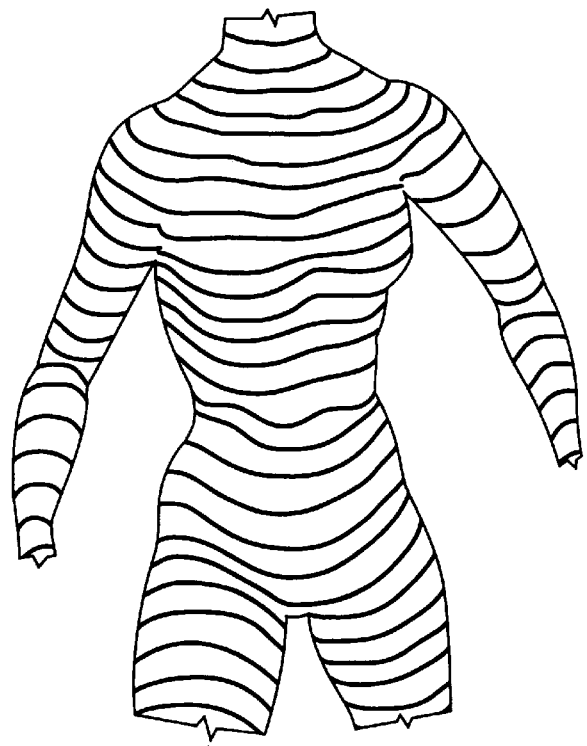
FIG. 3B illustrates the pattern of light having sinusoidally varying intensity of FIG. 3A projected onto a three-dimensional object.

When a pattern of light having sinusoidally varying intensity is projected onto a flat reference plane, the pattern appears as a series of straight parallel alternating light and dark fringes, as shown in FIG. 3A. Typically for PMP applications relating to body measurement, the period of the projected pattern as measured on the reference plane, is about thirty-five (35) millimeters (mm) and represents the width of an adjacent light and dark fringe. However, when the same pattern of light is projected onto a 3-D object, the fringes are deformed by the surface contour of the object and are no longer generally straight parallel, as shown in FIG. 3B.

Referring back to FIG. 1, both the deformed pattern from the 3-D object and the parallel pattern from the reference plane are captured by a CCD camera 16 which is interfaced with an image processing system 18. Although other types of cameras may be used, a CCD camera is preferable. An exemplary CCD camera is the PULNIX model TM-545W (PULNIX America, Inc., Sunnyvale, Calif.). In a preferred embodiment, a plurality of light projectors 12, selectively positioned relative to the 3-D object 14, project a sinusoidal pattern of light onto the entire surface of the object. Preferably, a plurality of CCD cameras 16 capture the image of the entire surface of the 3-D object 14 including the pattern of light projected thereon.

Each CCD camera 16 is interfaced with an image processing system 18 for displaying, via display 22, the captured image and for performing a variety of image processing functions. In addition, the image processing system 18 controls, via phase shift electronics 24, the translation stage supporting the light source 12 for shifting the phase of the projected sinusoidal pattern of light. As is known to those with skill in the art, the frame grabber 20 stores each image captured by the CCD camera 16 on an incremental time basis. The micro-computer 26 controls the image processing system 18 and generally decides when to capture, grab, display, and process an image. In addition, the micro-computer 26 controls the phase shifting of the sinusoidal light pattern via the phase shift electronics 24. Furthermore, the micro-computer 26 serves as the user's interface to the image processing system 18. Preferably, the image of the 3-D object, including the deformed pattern of fringes, is displayed via an array of pixels comprising 240 rows by 240 columns. However, as would be understood by those having skill in the art, other array configurations are acceptable. The micro-computer 26 is capable of processing and storing data for each pixel in the array, including optical phase and intensity values. Exemplary image processing systems are disclosed, for example, in *Digital Image Processing, A Practical Primer*, pp. 69–126, by Gregory A. Baxes, Cascade Press, 1984.

Figures 2, 4A:
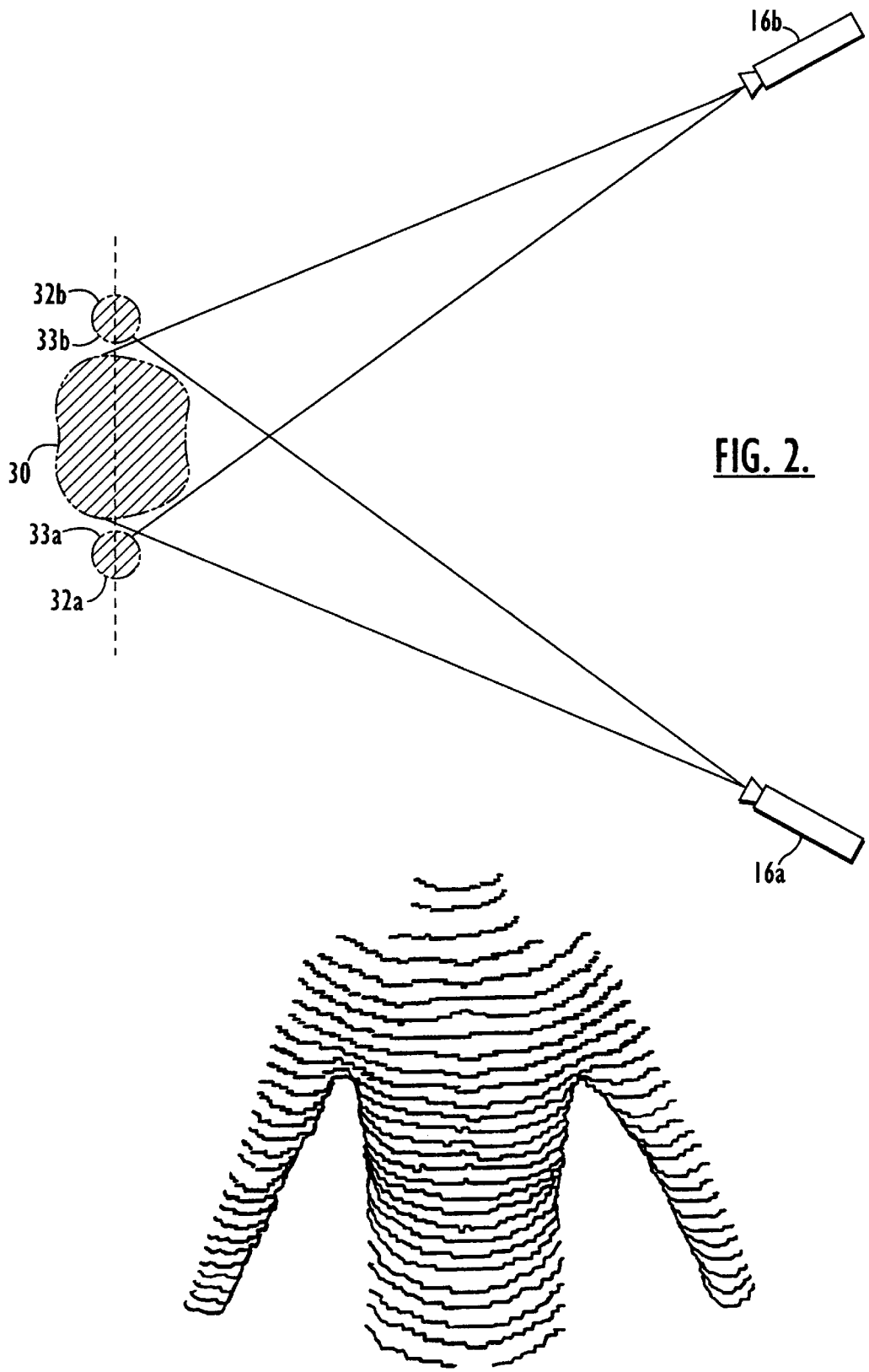
FIG. 2 is a sectional view taken along lines 2—2 in FIG. 1, illustrating surface discontinuities caused by the torso overlapping each arm and arm overlapping torso from the perspective of each camera.
FIG. 4A is an illustration of "xyz" data of a human body without a jump order problem.

Referring now to FIG. 2, a cross-sectional plan view of a human torso 30 having arms 32a, 32b on opposing sides is illustrated. Two CCD cameras 16a, 16b are positioned to record the image of the torso and arms from 30° on either side of the perpendicular, respectively. Although illustrated having a 30° angle with respect to the perpendicular, the CCD cameras 16a, 16b may be positioned at any one of a number of acceptable angles. From the viewpoint of each camera 16a, 16b, an arm is partially obscured by the torso 30. For example, from the perspective of camera 16a, a portion 33b of the arm 32b is obscured by the torso 30. Similarly, from the perspective of camera 16b, a portion 33a of the arm 32a is obscured by the torso 30. Consequently, camera 16a observes what appears to be a discontinuity in the surface of the torso 30, created by the overlap of the torso 30 with the arm 32b. Similarly, camera 16b observes what appears to be a discontinuity in the surface of the torso 30, caused by the overlap of the torso 30 and the arm 32a.

Figure 4B:
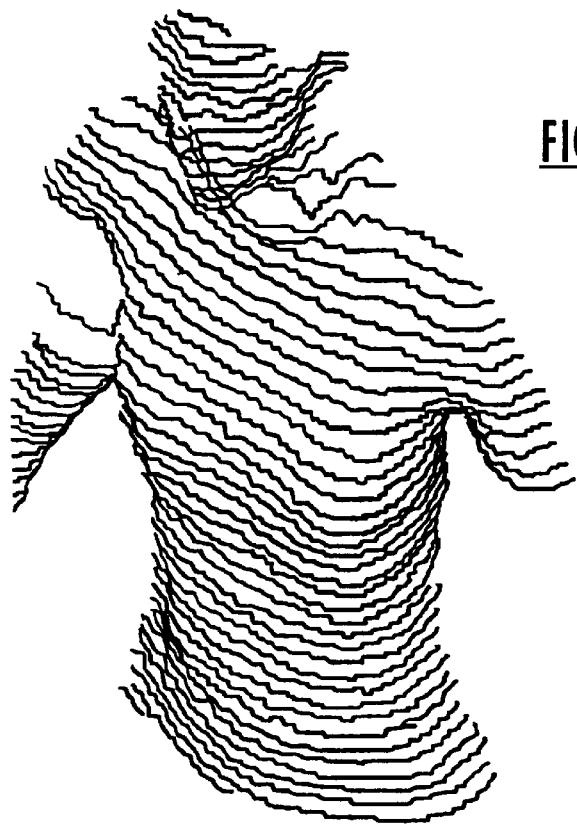
FIGS. 4B, 4C are illustrations of "xyz" data of a human body with a jump order problem.
Figure 4C:
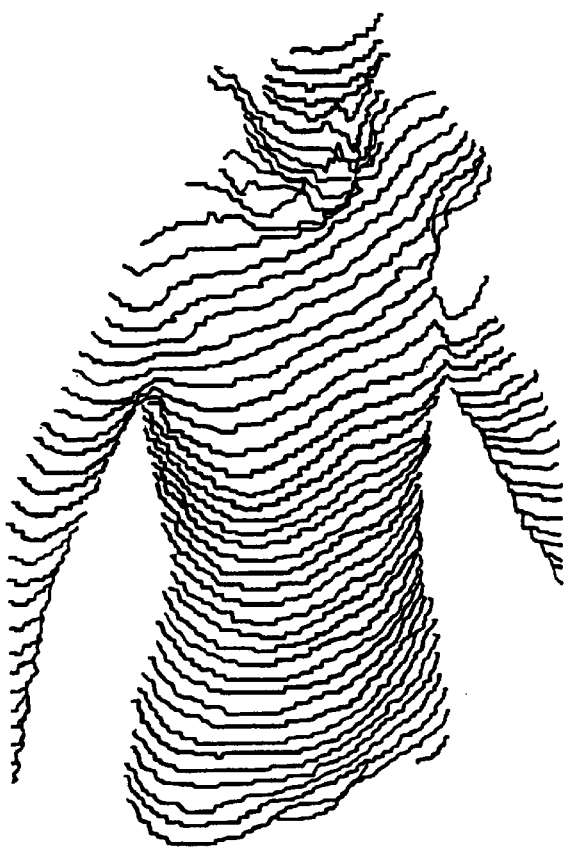

The apparent discontinuities produce ambiguous data from which accurate optical phase values cannot be determined for each arm 32a, 32b. This is illustrated graphically in FIGS. 4A, 4B, and 4C. FIG. 4A is xyz data of body by using PMP from the computer-generated image of the deformed pattern of fringes resulting from a pattern of light having sinusoidally varying intensity projected onto a human torso and arms as viewed from a direction perpendicular to the front of the torso 30. Because the torso 30 does not overlap the arms 32a, 32b from this perspective, the image processing system 18 (FIG. 1) is able to obtain accurate optical phase data for each pixel, as manifested by the continuous appearance of the dark lines. By contrast, as illustrated in FIGS. 4B and 4C, correct optical phase data is unavailable for each arm that is overlapped by the torso, as manifested by the absence of dark fringes in portions of each one of the arms 32a, 32b. Because optical phase data is unavailable for the regions adjacent the overlapping portions, a determination of the surface contour via PMP techniques cannot be performed with sufficient accuracy for the arms and areas adjacent the discontinuities. Furthermore, the optical phase data that is available for each one of the arms 32a, 32b is typically incorrect because of the discontinuity caused by the overlapping torso 30.

Surface contour measurement via PMP is disclosed in U.S. Pat. No. 4,641,972 to Halioua et al., and is incorporated herein by reference in its entirety. Illustrated schematically in FIG. 5A, the measurement of the surface contour of an object using PMP is known to those having skill in the art and is described hereinbelow only in general terms. A grating projector 12 having phase shifting capability, projects a pattern of light having sinusoidally varying intensity towards a 3-D object 14. The projected sinusoidal light pattern has a period $p_o$, as seen on the reference plane. The intensity that the light pattern produces at a point, for example C on the reference plane, can be calculated as follows:

$$I = a(x,y) + b(x,y)\cos(2\pi OC/p_o)$$

where a(x,y) is the background intensity, and b(x,y) is the fringe contrast. The point O represents the intersection of the imaging optical axis with the reference plane, and is assumed to coincide with an intensity maxima of the projected pattern. The expression $2\pi OC/p_o$ represents the phase at point C and effectively measures the geometric distance from point O to point C. A detector array 17 comprising a plurality of CCD cameras, interfacing with an image processing system (not shown) records and measures the intensity at point C on the reference plane and at point D on the surface of the object 14. The intensity at point D is the same as that at point A on the reference plane when modified by the reflectivity r(x,y) of the object 14. This is calculated as follows:

$$I_D = r_D[a_D + b_D \cos(2\pi OA/p_o)]$$

The difference between the phase value at point C ($\phi_C$) and the phase value at point D ($\phi_D$) observed by the camera 16, can be related to the geometric distance between point A and point C as follows:

$$AC = (p_o/2\pi)(\phi_C - \phi_D)$$

Figure 5A:
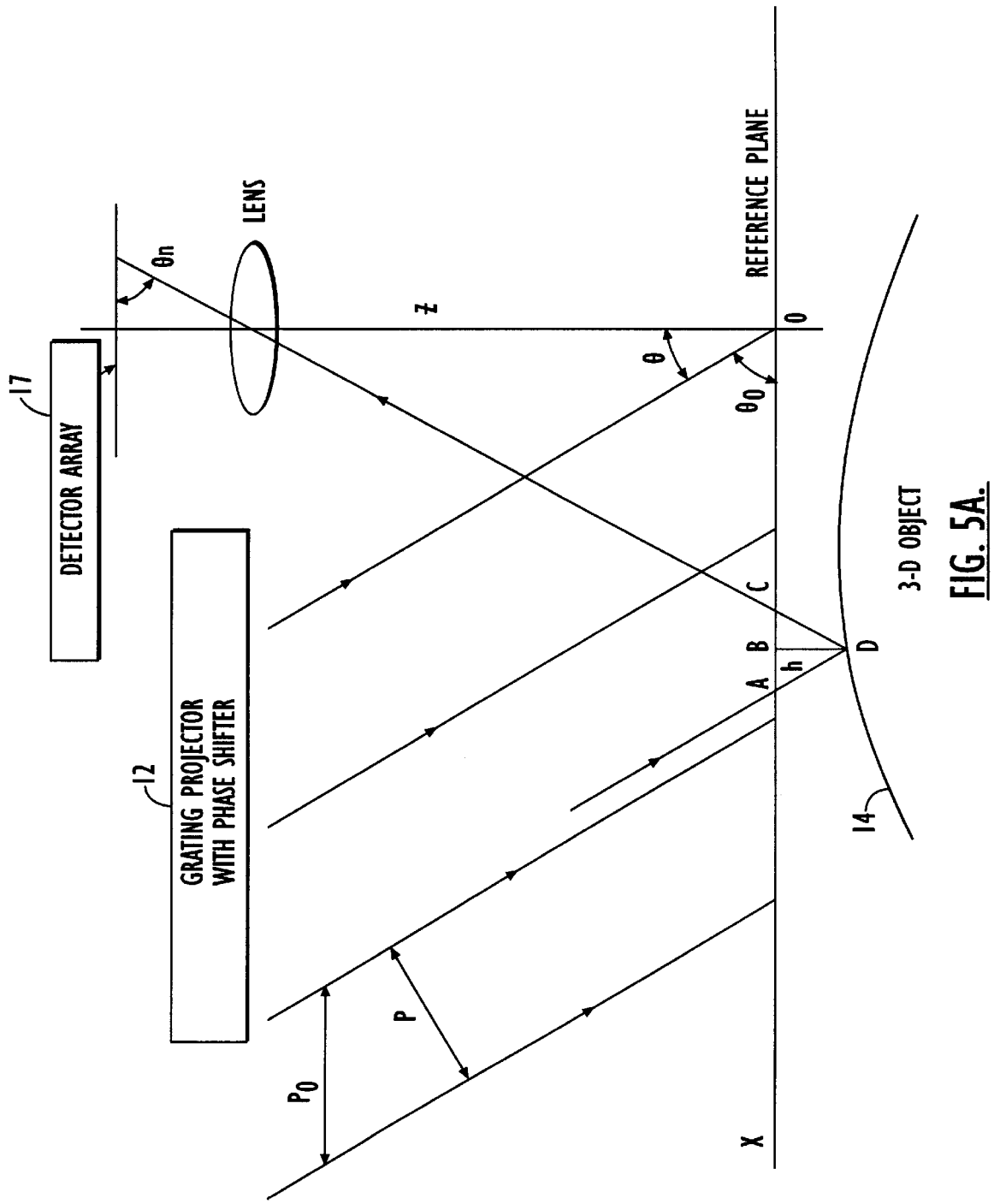
FIG. 5A illustrates the geometry involved in surface contour measurement of an object using PMP techniques.

The distance between point A and point C is related to the distance between point B and point D, which is the surface height h, as follows:

$$h = BD = (AC/2)\tan\theta_o/(1 + \tan\theta_o/\tan\theta_n)$$

where the angles $\theta_o$ and $\theta_n$ are as shown in FIG. 5A.

Because $\theta_n$ generally approximates 90°, the distance between point B and point D can be simplified as follows:

$$BD = h = (AC/2)\tan\theta_o$$

Figure 5B:
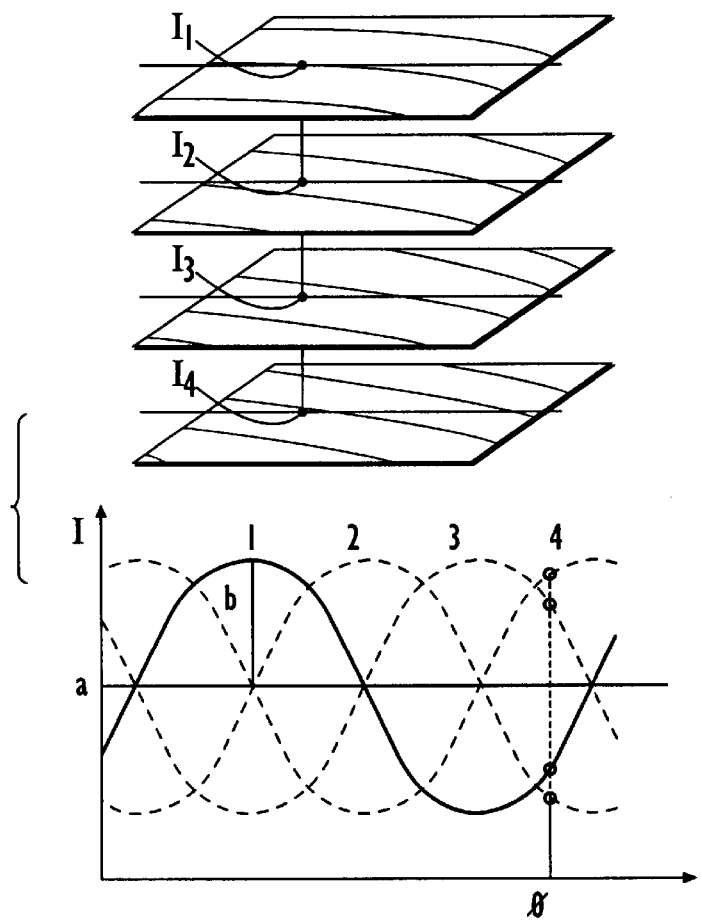
FIG. 5B illustrates four phase shifts of a beam of light having a sinusoidally varying intensity.

In order to distinguish between surface convexity and concavity, the slope at a particular point on the surface of the object 14 is determined by shifting the phase of the sinusoidal pattern of light by a predetermined amount. Typically, the phase is shifted in $2\pi/n$ increments and the intensity variation at a point on the reference plane and object 14, for example point C and point D, is measured and then stored within the micro-computer 26 (FIG. 1). As described previously, the $2\pi/n$ phase shifts are preferably achieved by operation of a motor-driven translation stage for each light projector 12. FIG. 5B schematically illustrates the intensity at a particular point for four $\pi/2$ shifts of the projected sinusoidal pattern.

Figure 5C:
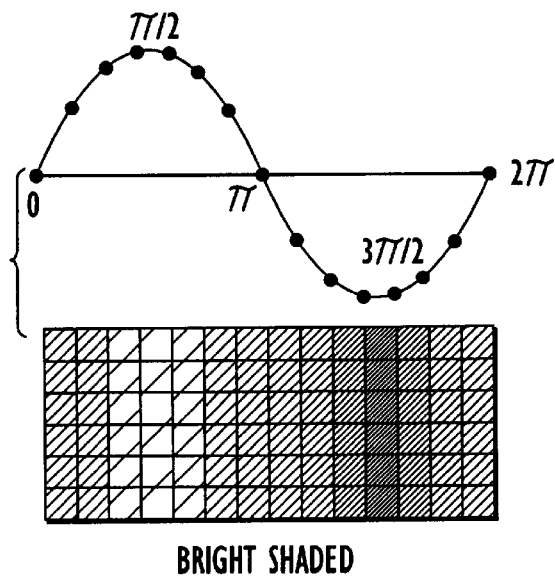
FIG. 5C illustrates one complete $2\pi$ period of a beam of light having sinusoidally varying intensity.

Referring now to FIG. 5C, the period or order of a sinusoidal pattern of light is schematically illustrated. One period of a sinusoidal pattern begins at 0 and ends at $2\pi$. Each particular point on the illustrated sine wave in FIG. 5C represents the local phase at that particular point. The light fringes are represented by the portion of the sine wave from 0 to $\pi$ and the dark or shaded fringes are represented by the portions of the sine wave from $\pi$ to $2\pi$. The point of highest intensity within a light fringe is $\pi/2$, conversely the point of lowest intensity within a dark fringe is $3\pi/2$.

Returning to FIG. 5A, intensity values at point D of object for each one of four phase shifts can be represented as follows:

$$I_{D1} = a_d + b_d \cos\phi$$

$$I_{D2} = a_d + b_d \cos(\phi + \pi/2)$$

$$I_{D3} = a_d + b_d \cos(\phi + \pi)$$

$$I_{D4} = a_d + b_d \cos(\phi + 3\pi/2)$$

The local phase $\phi_L$ at point D can then be computed as follows:

$$\phi_{DL} = \tan^{-1}\frac{(I_{D2} - I_{D4})}{(I_{D3} - I_{D1})}$$

The phase $\phi_{DL}$ is the same as the phase $\phi_{AL}$ in the reference plane:

$$\phi_{AL} = \phi_{DL}$$

Still referring to FIG. 5A, intensity values at point C of the reference plane for each of the four phase shifts can be represented as follows:

$$I_{C1} = a_C + b_C \cos\phi$$

$$I_{C2} = a_C + b_C \cos(\phi + \pi/2)$$

$$I_{C3} = a_C + b_C \cos(\phi + \pi)$$

$$I_{C4} = a_C + b_C \cos(\phi + 3\pi/2)$$

The local phase $\phi_L$ for point C can then be computed as follows:

$$\phi_{CL} = \tan^{-1}\frac{(I_{C2} - I_{C4})}{(I_{C3} - I_{C1})}$$

Local phase information is calculated and stored for each point on the object 14 represented by a pixel in the displayed image. Similarly, local phase information is calculated and stored for each point on the reference plane represented by a pixel in the corresponding displayed image of the reference plane.

The height h at each point on the object represented by a pixel in the displayed image is then determined as follows:

$$AC = (P_o/2\pi)(\phi_{AL} - \phi_{CL})$$

$$h = (AC/2)\tan\theta_o$$

Additionally, to each point on the object represented by a pixel in the displayed image, a phase order m is assigned. The phase order represents each complete $2\pi$ period of the sinusoidal pattern. For example, a phase order of 0 is assigned to the first complete period beginning at 0 and ending at $2\pi$. A phase order of 1 is assigned to the next complete period beginning at $2\pi$ and ending at $4\pi$, and so forth.

Thus, for a particular object having a sinusoidal pattern of light projected thereon, the image processing system 18 proceeds on a pixel-by-pixel basis and performs the following steps in a typical PMP process. The first step is to calculate and store the optical phase for each point on a 3-D object represented by a pixel. The next step is to recall the optical phase that was calculated and stored previously for each point on a reference plane represented by a corresponding pixel. The final step is to calculate the height of each point on the 3-D object relative to the reference plane and thereby determine the surface contour of the object.

Figure 6:
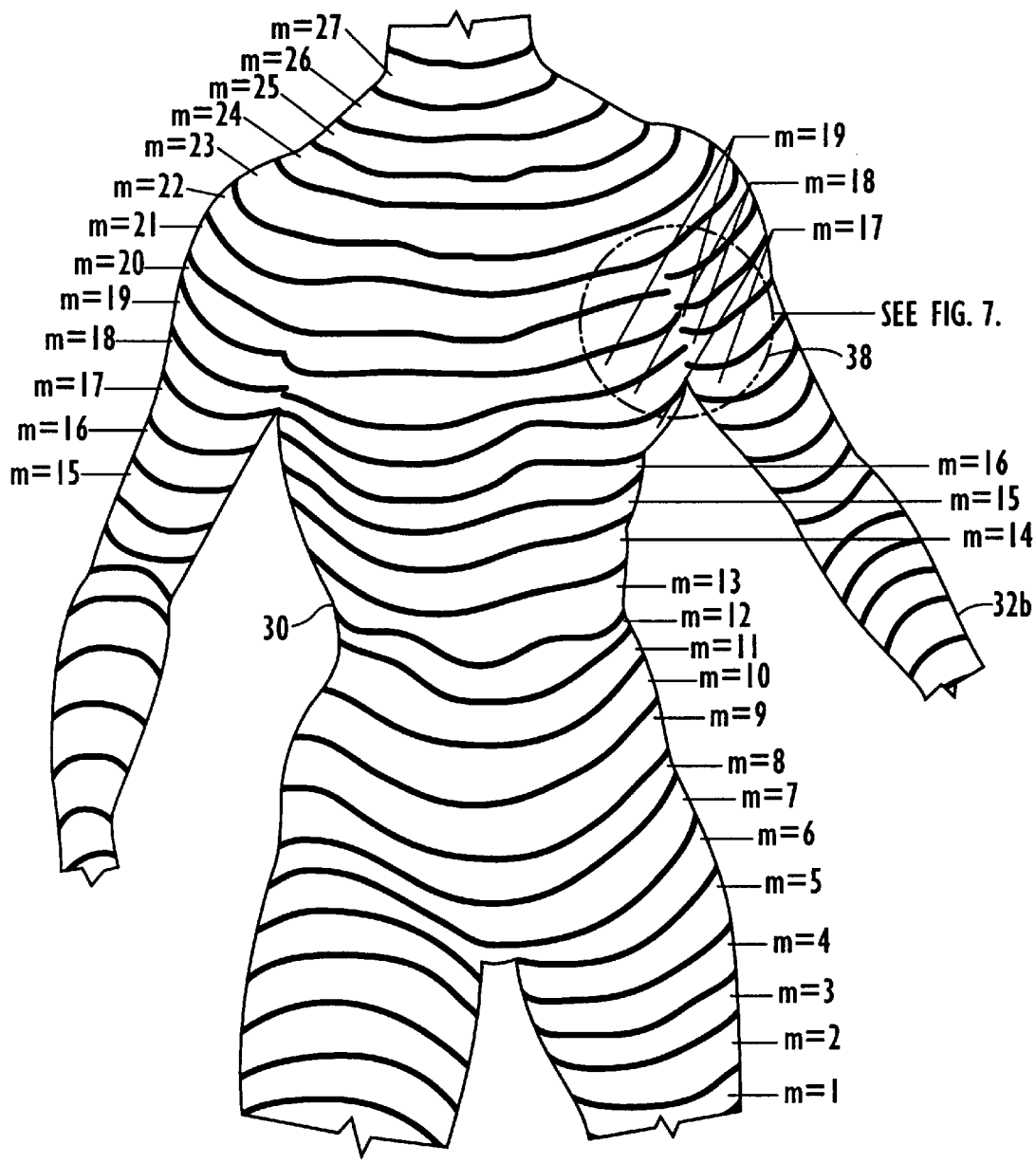
FIG. 6 illustrates a human body having a deformed pattern of light projected thereon, wherein each fringe is assigned an optical phase order value.

Referring now to FIG. 6, a 3-D object 14 with a pattern of light having sinusoidally varying intensity projected thereon is illustrated with a phase order M assigned to each $2\pi$ period of the pattern. As illustrated, the light and dark fringes are not continuous in certain areas. The fringes are not continuous in the left under-arm area 38 because the torso 30 appears to overlap the left arm 32b from the perspective of the camera recording this particular image. To the image processing system 18, the area of overlap 38 appears as a discontinuity in the surface of the 3-D object. Consequently, optical order values are unascertainable or incorrect for pixels along and adjacent the discontinuity. Because optical order values are not available or are inaccurate, the surface contour cannot be measured accurately for the arm 32b or for the area adjacent the region of overlap 38.

Figure 7:
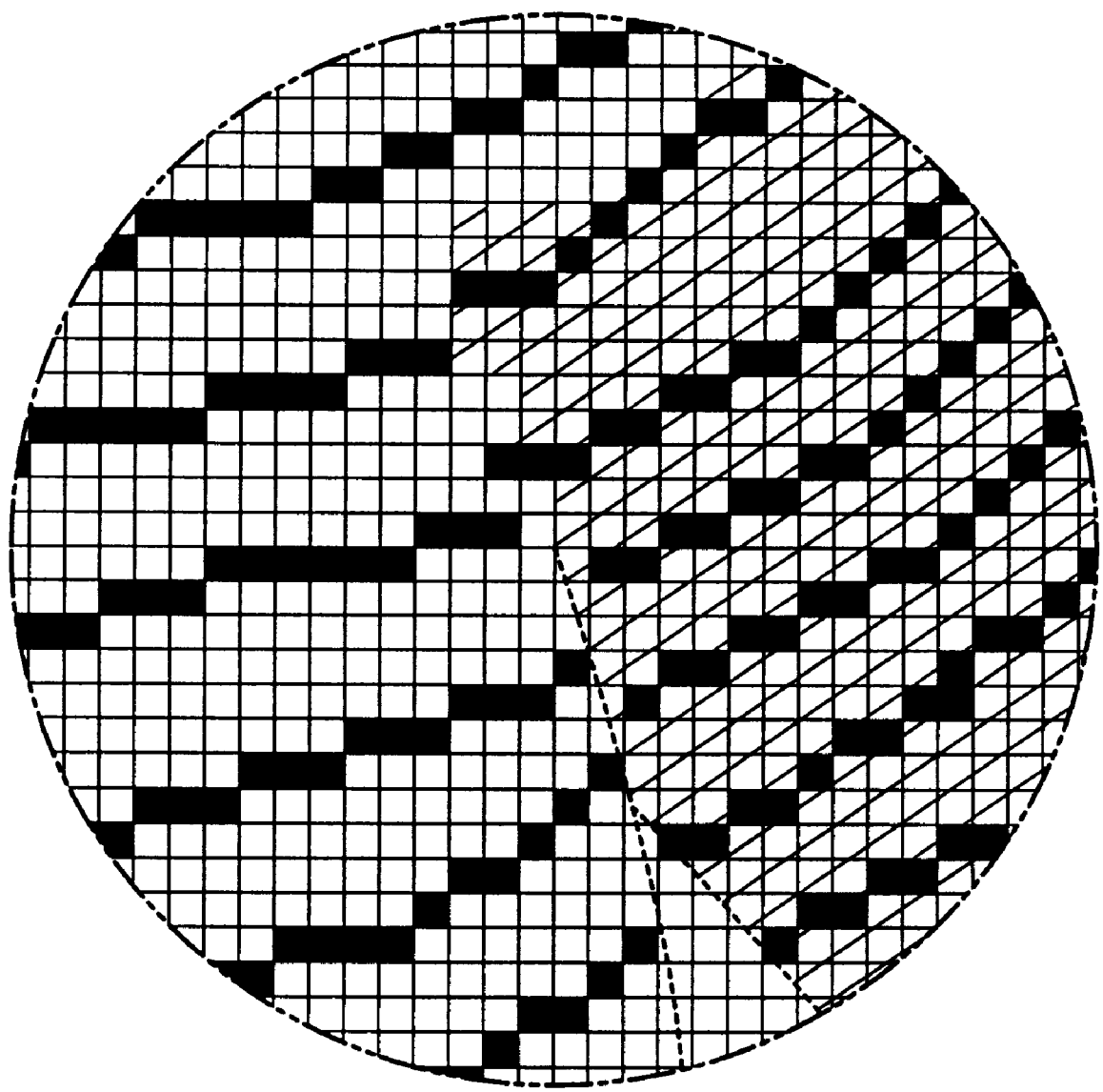
FIG. 7 is an enlarged view of the computer-generated image of the area of overlap illustrated in FIG. 6.

Referring to FIG. 7, the region of overlap 38 from FIG. 6 is represented by an array of pixels as captured by a CCD camera. Shaded pixels represent those pixels in the image for which optical phase values are unobtainable and/or incorrect, and for which the surface contour of the arm 32b cannot be calculated correctly by PMP techniques.

Figure 8:
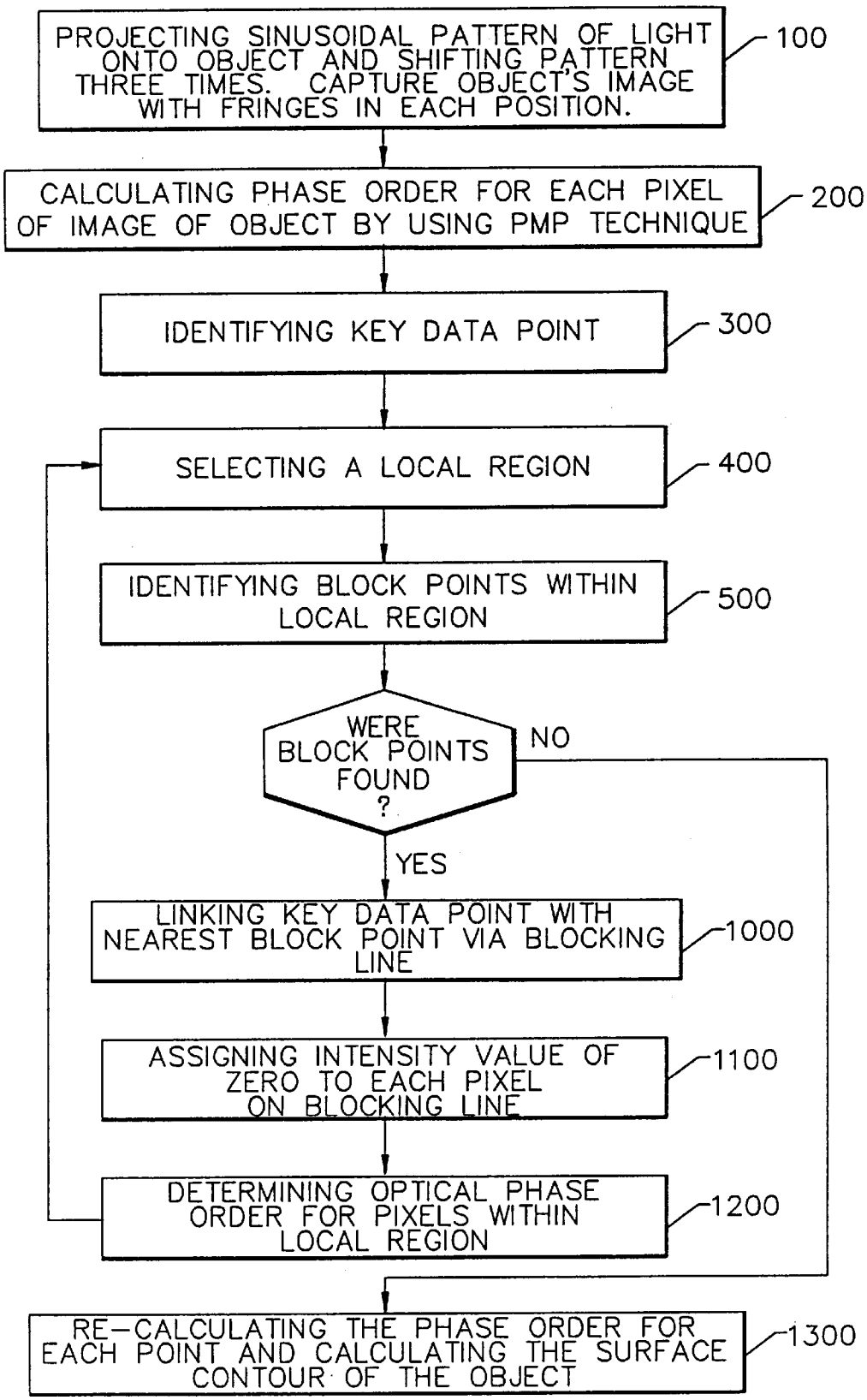
FIG. 8 is a flow chart of operations for obtaining the surface contour of an object having surface discontinuities, according to the present invention.

Referring now to FIG. 8, operations for obtaining the surface contour of a 3-D object in regions adjacent apparent discontinuities, according to the present invention, are described in detail. It will be understood that these operations may be performed by microcomputer, such that the microcomputer operates as means for performing the various functions and carries out the methods of the various operations. The various data generated for each pixel, and the various calculations involving this data may be processed, performed, and stored by microcomputer, or under other computer control. The stored program operations also act as computer readable code means.

The illustrated operations comprise projecting a pattern of light having a sinusoidally varying intensity onto a 3-D object (Block 100); calculating the order for each pixel of the image of the 3-D object using PMP techniques (Block 200); identifying a key data point (Block 300); selecting a local region containing an apparent discontinuity (Block 400); identifying block points within the local region (Block 500); determining whether block points were found (Block 600); linking the key data point with the block points via a blocking line (Block 1000); assigning intensity order of zero (0) to pixels located on the blocking line (Block 1100); calculating optical phase orders for the pixels in local search region (Block 1200); repeating Block 400 through Block 1200 until no block points are found; and re-calculating the phase order for each point and calculating the correct surface contour of the object using PMP techniques (Block 1300).

Figure 9:
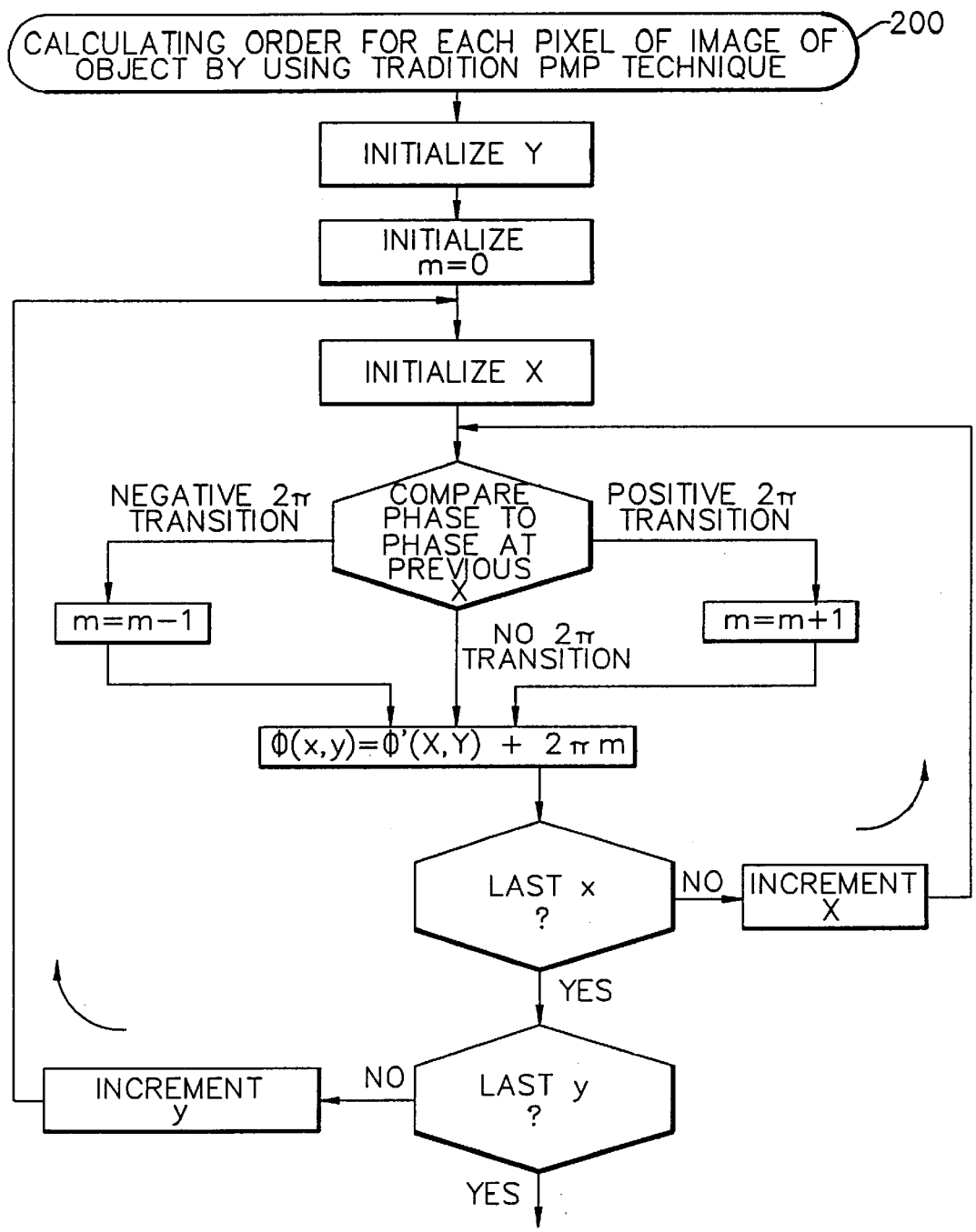
FIG. 9 is a flow chart of phase order assignment in PMP technique for calculating the surface contour of an object.

Referring now to FIG. 9, a process for calculating the optical phase order of pixels comprising an image of a 3-D object (Block 200) is illustrated. This method is the PMP technique disclosed in the previously mentioned U.S. Pat. No. 4,641,972 to Halioua et al.

Figure 10:
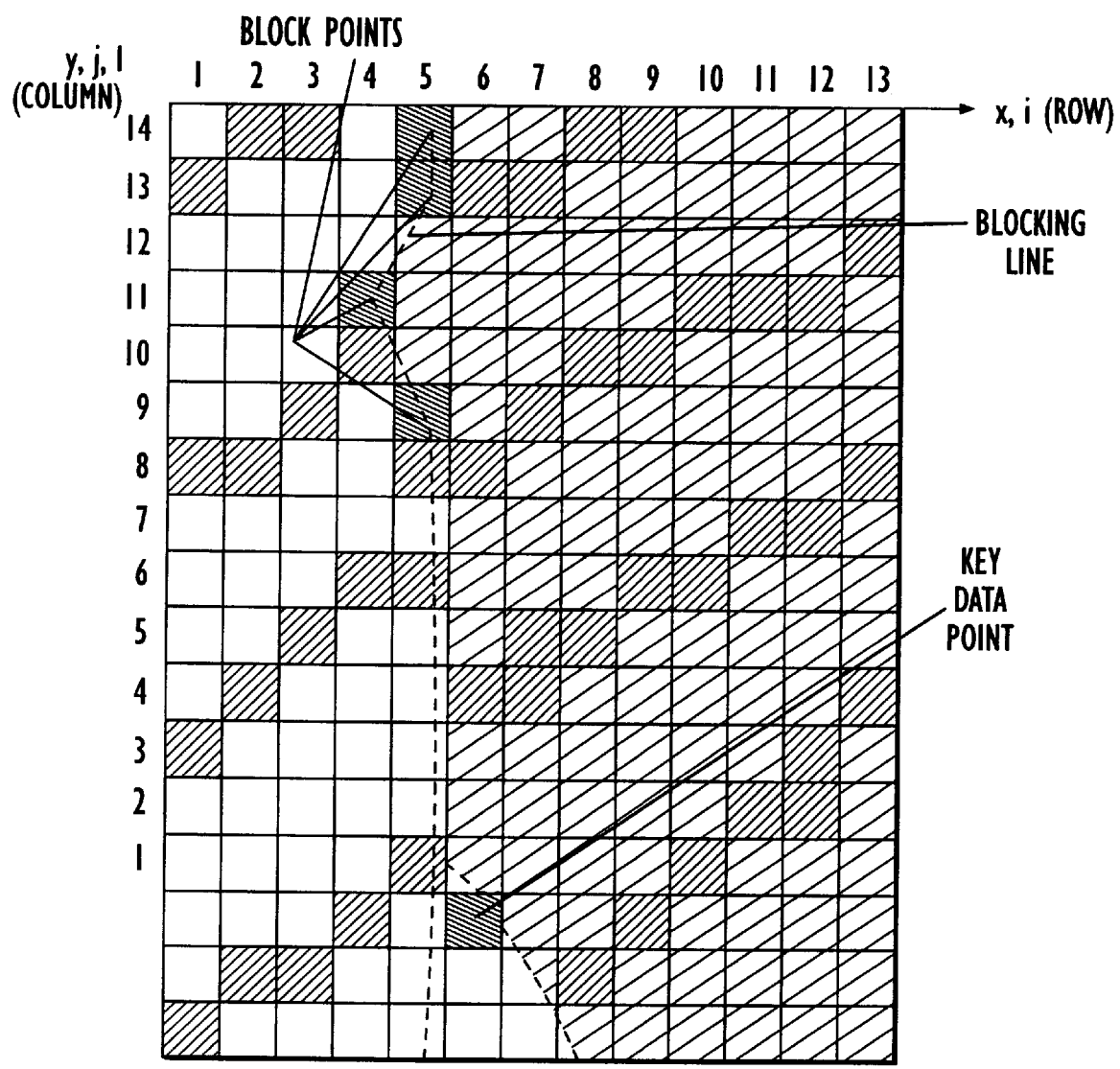
FIG. 10 illustrates a sub-array of pixels comprising the local region of the computer-generated image illustrated in FIG. 7.

Referring now to FIG. 10, selecting a local region (Block 300) comprises selecting a sub-array of pixels including pixels for which invalid or ambiguous data is contained. This sub-array will typically comprise the region of an apparent discontinuity. The sub-array comprises pixels in the area of overlap between torso 30 and arm 32b. The X-axis and Y-axis are arranged with respect to the torso 30 and arm 32b as illustrated in FIG. 10. Each row and column of the sub-array are numbered. Pixels along the Y-axis will also be identified by the subscripts j and l in the steps for locating blocking points described in detail below. Pixels along the X-axis will also be identified by the subscript i in the steps for locating block points. In the selected local region, the key data point is where torso 30 and arm 32 first appear to overlap from the perspective of the camera taking the particular image. This corresponds to a pixel having x,y coordinates of 5,8 ($P_{5,8}$) in FIG. 10.

Figure 11:
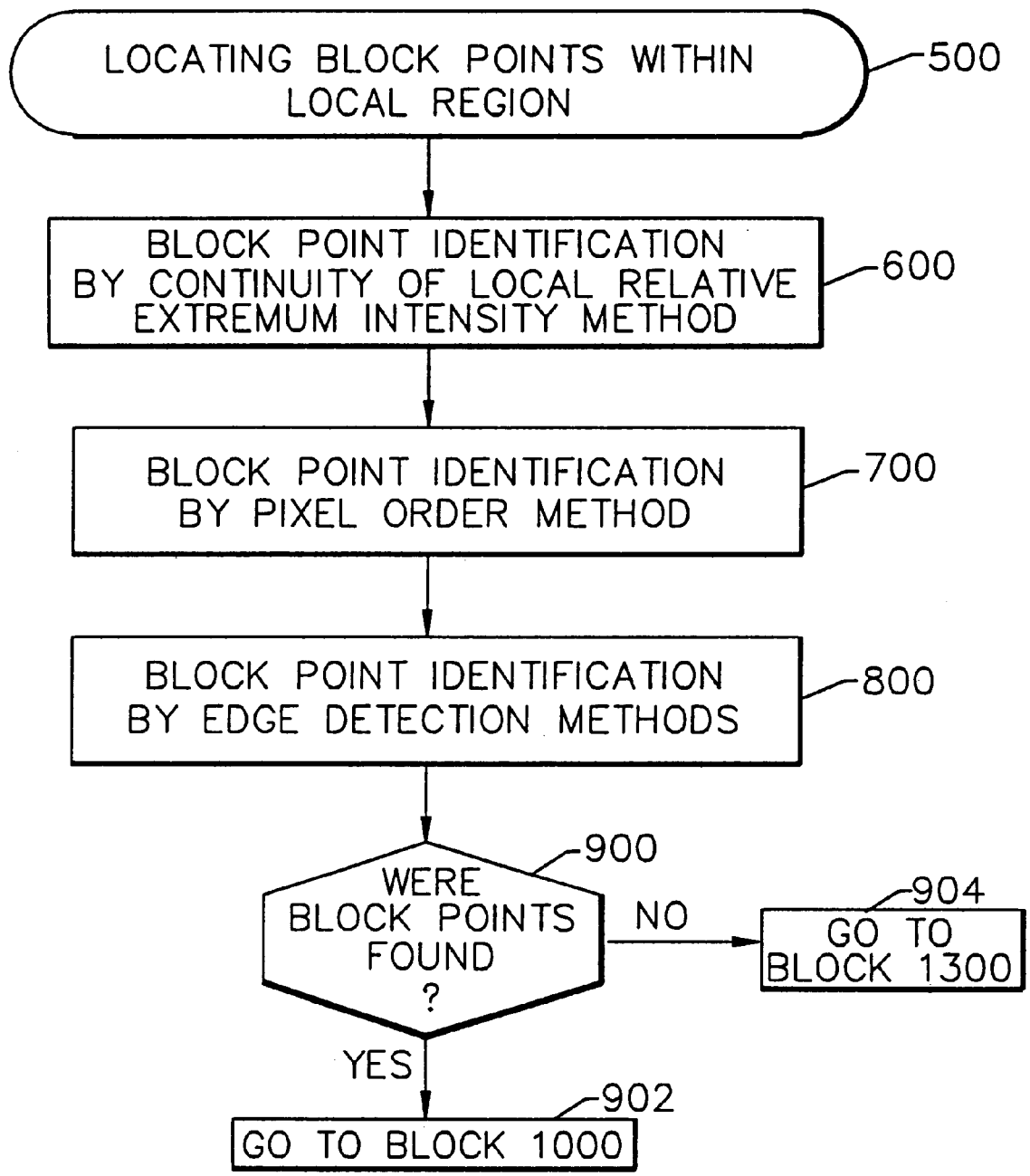
FIG. 11 is a flow chart illustrating the combination of methods for identifying block points, according to the present invention.

After the key data point for a local region is identified, pixels designated as block points are identified within the local region (Block 500). The term "block point," as used herein, refers to some points that are near to or in the separate edge between two portions that are discontinuous. Referring now to FIG. 11, the combination of methods for block point identification, according to the present invention, are illustrated schematically. In the first method, block points are identified by a continuity of local relative extremum intensity method (Block 600). Next, block points are identified by a pixel order method (Block 700). Finally, block points are identified by a combination of various edge detection methods (Block 800). It is understood, however, that the order in which these methods proceed is not important. The present invention facilitates the identification of existing block points via the unique combination of identification methods represented by Blocks 600, 700, and 800. A greater percentage of existing block points can be identified using this combination of methods than from existing methods, alone. Therefore, Blocks 600, 700, and 800 may proceed in any order desirable. After all the block point identification methods have been utilized, a determination is made whether any block points were found (Block 900). If no block points were identified, the process is terminated (Block 904). If, however, block points were identified, the process proceeds to Block 902 whereby the key data point identified in (Block 400) is linked with the nearest identified block point (Block 1000).

Figure 12:
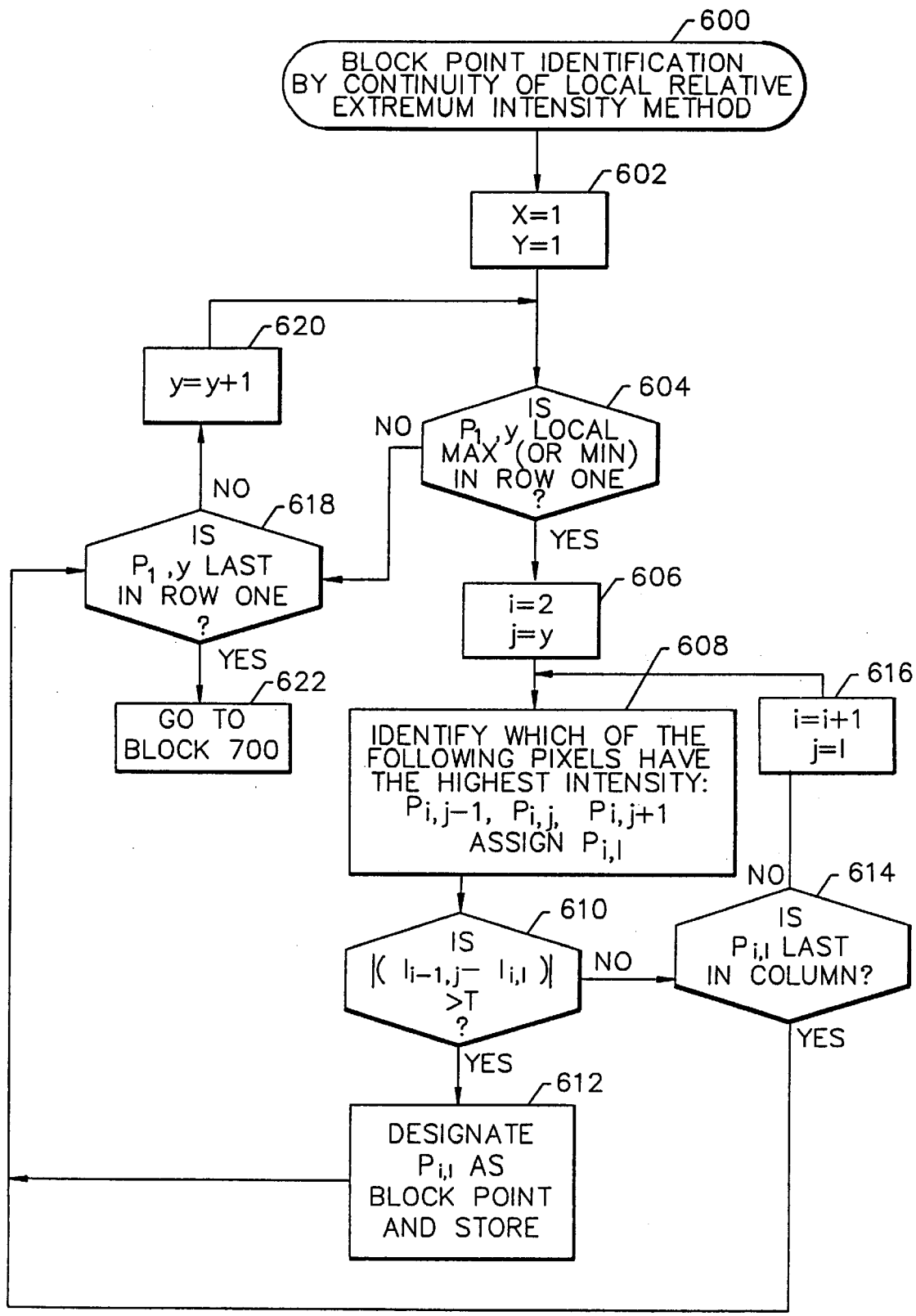
FIG. 12 is a flow chart illustrating block point identification by the continuity of local relative extremum intensity method, according to the present invention.

Referring now to FIG. 12, block point identification by the continuity of local relative extremum intensity method (Block 600), according to the present invention, is described in detail. Initially, the coordinates x and y are each assigned the value of one (1) (Block 602). Beginning with the pixel having x,y coordinates of 1,1 ($P_{1,1}$) in the sub-array illustrated in FIG. 10, a determination is made as to whether this particular pixel has an intensity value that is a local maximum or minimum in its row (Block 604). If this pixel does not have an intensity value that is a local maximum or minimum in its row, a determination is then made whether this pixel is the last pixel in this particular row (Block 618). If the pixel is not the last pixel in the row, the y coordinate is incremented by 1 (Block 620) and a determination is then made whether pixel $P_{1,y+1}$ is a local maximum or minimum on the row (Block 604). Assuming that no pixel in the row is found to be a local maximum or minimum, the continuity of local relative extremum intensity method terminates (Block 622) and the process proceeds to the pixel order method (Block 700).

Returning now to Block 604, if a pixel is found to be a local maximum or minimum, i is assigned the value of 2 and j is assigned the value of y (Block 606). The three closest pixels to this pixel on the next row (x+1) are then analyzed (Block 608) and the one with the highest (or lowest) intensity is identified. For example, if $P_{1,2}$ is found to be a local maximum in Block 604, the three pixels $P_{2,1}$, $P_{2,2}$, $P_{2,3}$ are analyzed and the pixel with the highest (or lowest) intensity is designated as $P_{i,l}$. The intensity of $P_{i,l}$ is subtracted from the intensity of $P_{i-1,j}$, and the absolute value of this quantity is compared with a threshold value T (Block 610). If the absolute value of difference is greater than the threshold, the pixel $P_{i,l}$ is designated as a block point and stored in the micro-computer 26 (Block 612). If the absolute value of difference is not greater than the threshold, a determination is made whether pixel $P_{i,l}$ is the last pixel in the column y (Block 614). If $P_{i,l}$ is the last pixel in the column, a determination is then made whether it is the last pixel in the row x (Block 618). It should be noted that the coordinates i,l are interchangeable with the x,y coordinates throughout the continuity of local relative extremum intensity method. Furthermore x and i are interchangeable and y, j, and l are interchangeable throughout the continuity of intensity method.

If $P_{1,y}$ is the last pixel in row 1, the method is terminated (Block 622). If $P_{1,y}$ is not the last pixel in row 1, y is incremented by one (1) (l and y are interchangeable) (Block 620). A determination is made when new pixel $P_{1,y}$ is a local maximum or minimum in row 1 (Block 604) and the entire continuity of local relative extremum intensity procedure previously described continues.

Returning to Block 614, if $P_{i,l}$ is not the last pixel in the column, i is incremented by one (1) and j is assigned the value of 1. By way of illustration, assuming that pixel $P_{2,3}$ was designated $P_{i,l}$ previously in Block 608, after incrementation, $P_{i,j}$ becomes $P_{3,3}$. As described above, the three closest pixels to this pixel on the next row are then analyzed (Block 608) and the one with the highest intensity is identified and designated as new pixel $P_{i,l}$. For example, the three pixels nearest old pixel $P_{i,l}$ ($P_{2,3}$) on the next row are $P_{3,2}$, $P_{3,3}$, and $P_{3,4}$. These pixels are analyzed and the one with the highest (or lowest) intensity is designated new pixel $P_{i,l}$.

The remainder of the sub-array is systematically analyzed using the steps of the continuity of local relative extremum intensity method described above and illustrated in FIG. 12. Identified block points are so designated and stored via the micro-computer 26 (FIG. 1). Upon termination of the continuity of local relative extremum intensity method at Block 622, the process proceeds with identifying block points via the pixel order method (Block 700).

Figure 13A:
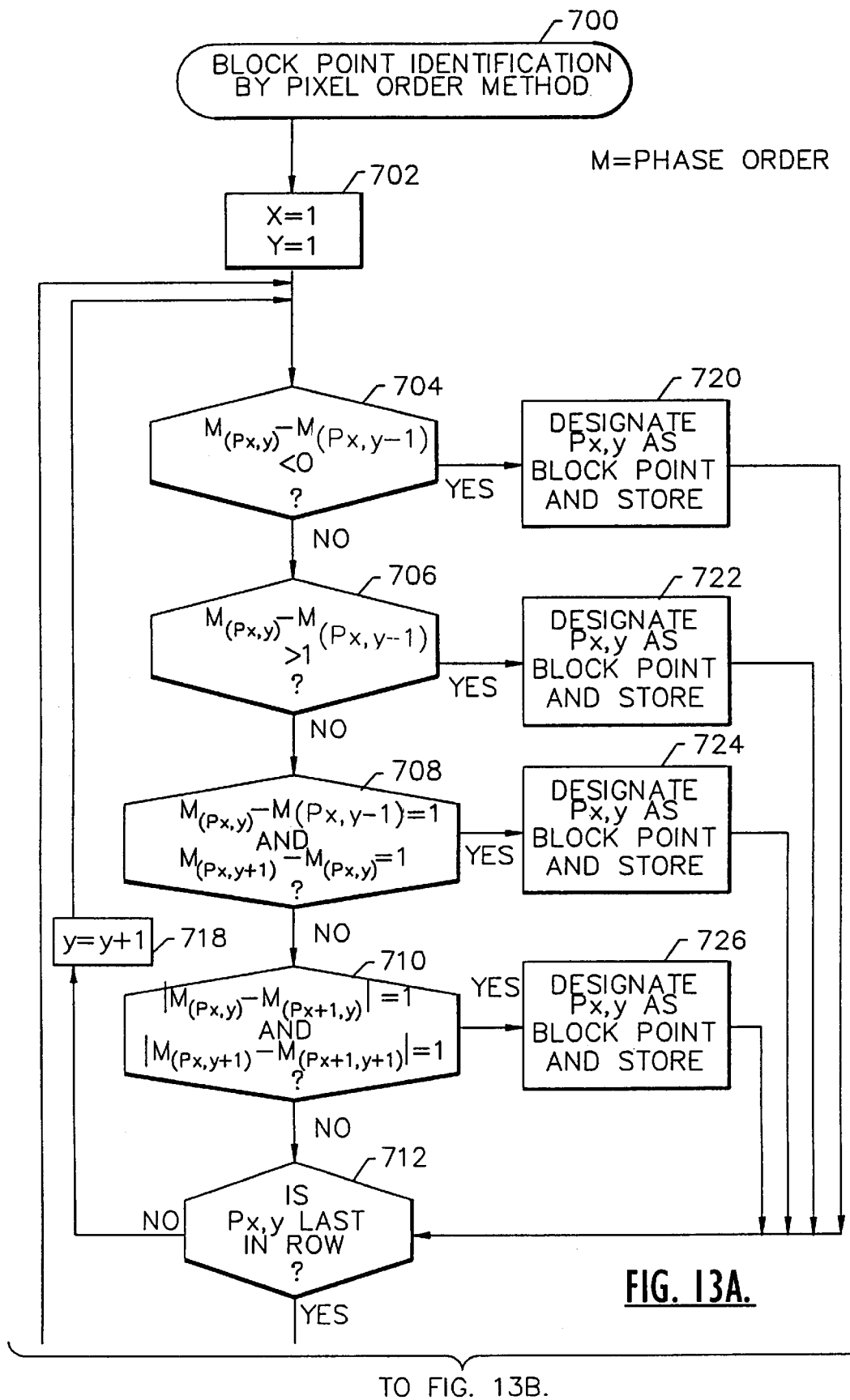
FIGS. 13A, 13B are flow charts illustrating block point identification by the pixel order method, according to the present invention.
Figure 13B:
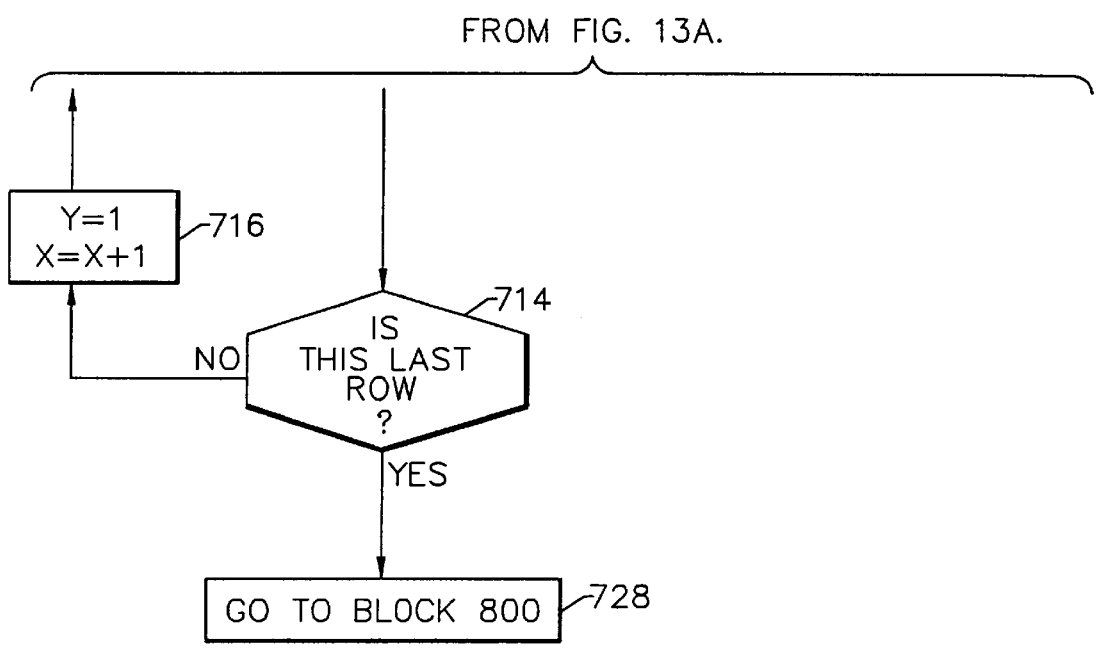

Referring now to FIGS. 13A and 13B, block point identification by the pixel order method (Block 700), according to the present invention, is described in detail. Initially, the coordinate x and y are each assigned the value of one (1) (Block 702). Beginning with the pixel having x,y coordinates of 1,1 ($P_{1,1}$) in the sub-array illustrated in FIG. 10, a determination is made whether the phase order M of $P_{x,y}$ minus the phase order of pixel $P_{x,y-1}$ is less than zero (Block 704). Thus, the phase order of $P_{1,1}$ ($M(P_{1,1})$) minus the phase order of $P_{1,0}$ ($M(P_{1,0})$) is calculated and compared with zero. If the quantity $M(P_{1,1})-M(P_{1,0})$ is less than zero, the pixel $P_{x,y}$ (here $P_{1,1}$) is designated as a block point and stored (Block 720) and the method proceeds to Block 712. If the quantity $M(P_{1,1})-M(P_{1,0})$ is not less than zero, then the method proceeds to Block 706.

At Block 706, the quantity $M(P_{x,y})-M(P_{x,y-1})$ is calculated and compared with one. If the quantity is greater than one, the pixel $P_{x,y}$ (here $P_{1,1}$) is designated as a block point and stored (Block 722) and the method proceeds to Block 712. If the quantity $M(P_{x,y})-M(P_{x,y-1})$ is not greater than one, then the method proceeds to Block 708.

At Block 708, two quantities are calculated and compared. First, the quantity $M(P_{x,y})-M(P_{x,y-1})$ is calculated and compared with one. Next, the quantity $M(P_{x,y+1})-M(P_{x,y})$ is calculated and compared with one. If both quantities equal one, the pixel $P_{x,y}$ (here $P_{1,1}$) is designated as a block point and stored (Block 724) and the method proceeds to Block 712. If either one or both of the quantities is not equal to one, then the method proceeds to Block 710.

At Block 710, two quantities are calculated and compared. First, the quantity $|M(P_{x,y})-M(P_{x+1,y})|$ is calculated and compared with one. Next, the quantity $|M(P_{x,y+1})-M(P_{x+1,y+1})|$ is calculated and compared with one. If both quantities equal one, the pixel $P_{x,y}$ (here $P_{1,1}$) is designated as a block point and stored (Block 726) and the method proceeds to Block 712. If either one or both of the quantities is not equal to one, then the method proceeds to Block 712.

At Block 712, a determination is made whether pixel $P_{x,y}$ is the last pixel in the row. If not, Y is incremented by 1 such that $P_{x,y}$ now equals $P_{x,y+1}$ (Block 718), and the steps represented by Blocks 704, 706, 708, and 710 are repeated for this new pixel. If the pixel $P_{x,y}$ is the last pixel in the row, the method proceeds to Block 714 where a determination is made whether the current row is the last row in the sub-array. If this is the last row, the method is terminated (Block 728) and the block point identification process proceeds to Block 800. If this is not the last row, x is incremented by one (1) and y is assigned the value of one (1) (Block 716) and the steps represented by Blocks 704, 706, 708, and 710 are repeated for the new pixel $P_{x+1,y}$.

The pixel order method illustrated in FIGS. 13A and 13B progresses on a systematic basis through the sub-array until the phase order of each pixel has been compared according to Blocks 704, 706, 708, and 710. As an illustrative example, assume $P_{x,y}$ is $P_{4,4}$ and its phase order is 6. Also assume that the phase order for $P_{x,y-1}$ ($P_{4,3}$) is 4. The quantity $M(P_{4,4})-M(P_{4,3})$ equals 2 (6–4). Pixel $P_{4,4}$ would not be designated as a block point according to Block 704, but would be designated a block point according to Block 706.

Further illustrating the pixel order method, assume $P_{x,y}$ is $P_{4,4}$ and its phase order is 3, also assume that the phase order of pixel $P_{x,y-1}$ is 2 and that the phase order of pixel $P_{x,y+1}$ is 4. The quantity $M(P_{4,4})-M(P_{4,3})$ equals 1 (3–2) and the quantity $M(P_{4,5})-M(P_{4,4})$ equals 1 (4–3). As a result pixel $P_{4,4}$ would be designated a block point according to Block 708.

Assume $P_{x,y}$ is $P_{4,4}$ and its order is 4. Also assume that the phase order of $P_{x+1,y}$ ($P_{5,4}$) equals 3, the phase order of $P_{x,y+1}$ ($P_{4,5}$) equals 4, and the phase order of $P_{x+1,y+1}$ ($P_{5,5}$) equals 3. The quantity $M(P_{x,y})-M(P_{x+1,y})$ equals 1 (4–3), and the quantity $M(P_{x,y+1})-M(P_{x+1,y+1})$ equals 1 (4–3). As a result, pixel $P_{4,4}$ is designated as a block point according to Block 710.

Figure 14:
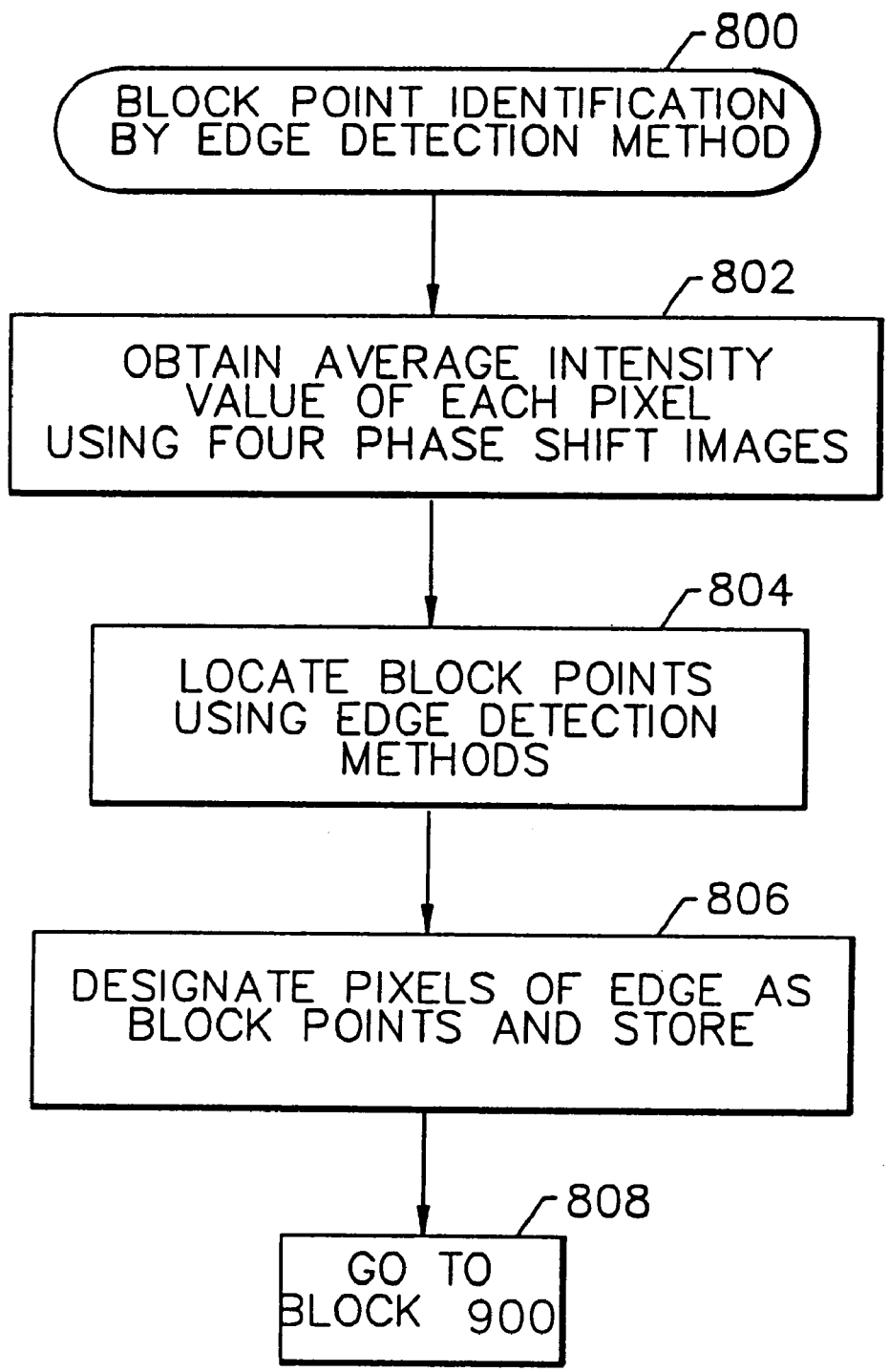
FIG. 14 is a flow chart illustrating block point identification by an edge detection technique.

Referring now to FIG. 14, the final method of identifying block points in the local region utilizes traditional edge detection techniques. A variety of edge detection methods are known and are disclosed in *Digital Image Processing A Practical Primer*, by Gregory A. Baxes, pp. 52–56, 1984. Prior to using an edge detection technique, the average intensity for each pixel in the sub-array (FIG. 10) is calculated using four phase shift images described above (Block 802). Utilizing the average intensity for each pixel, traditional edge detection techniques are used to determine block points in the sub-array, which are then designated as such and stored (Block 806). In a typical edge detection technique, for example, the image is shifted, either horizontally or vertically, by one pixel, and then the row or column containing the pixel is subtracted from the image. As is known to those having skill in the art, the image may be shifted in both the horizontal and vertical directions. Edge enhancement techniques produce images having sharp edge details. Still referring to FIG. 14, the identification of block points in the sub-array is complete at this point and the process advances to Block 900 (Block 808). Referring back to FIG. 11, if no block points were found, the process advances to Block 1300 (Block 904). If block points were found, the process advances to Block 1000 (Block 902).

Figure 15:
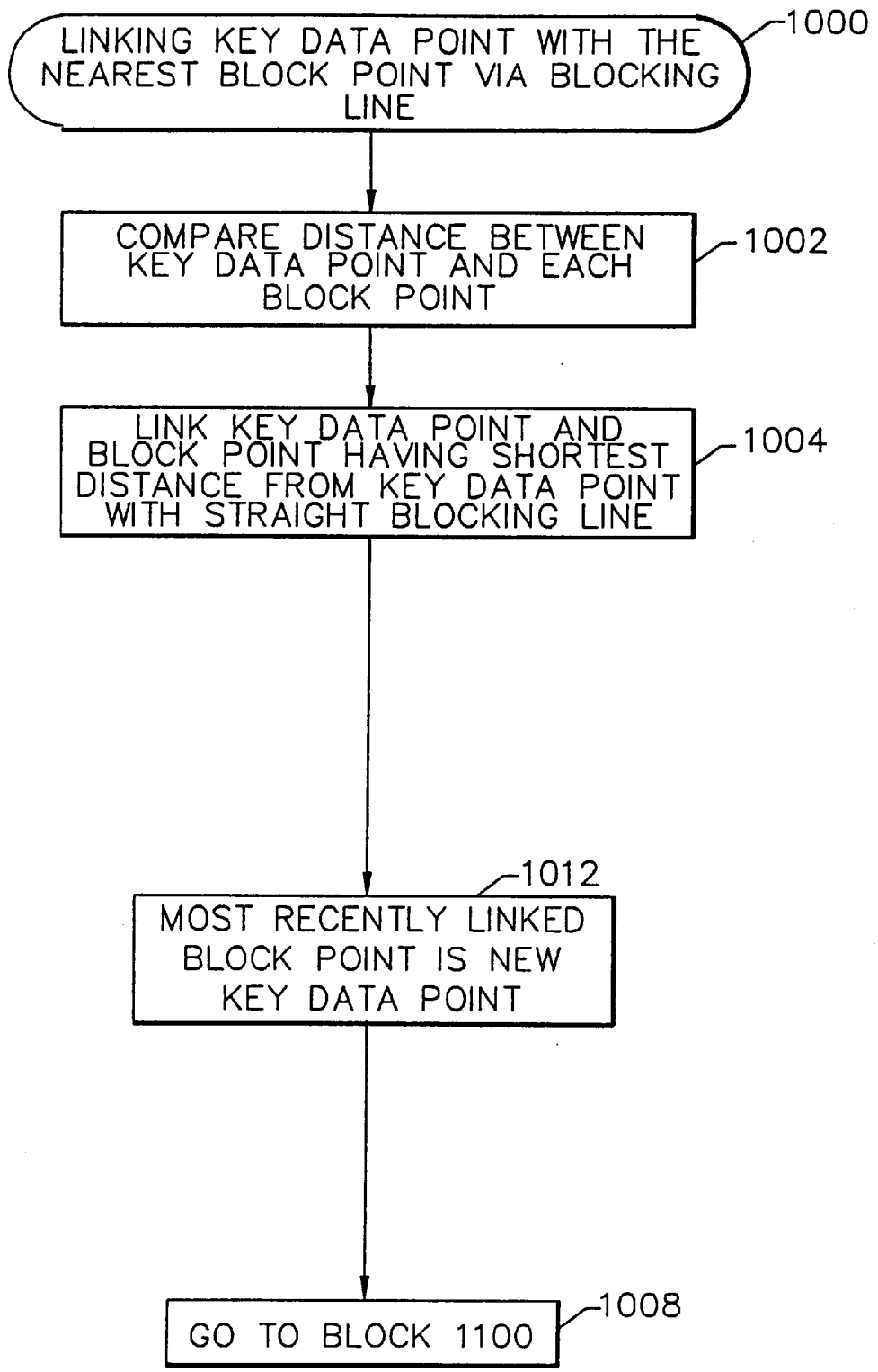
FIG. 15 is a flow chart illustrating the linking of a key data point and identified block points.

Referring now to FIG. 15, the linking of the nearest designated block point with the key data point (Block 1000) preferably comprises an iterative process of calculating and comparing distances between pixels. Initially, the distance between the key data point and each of the block points is calculated and compared (Block 1002). Next, the block point closest to the key data point is linked to the key data point with a straight line (Block 1004). The most recently linked block point is identified as the new key data point (Block 1012). The linking of block points is terminated (Block 1008), and the process is advanced to Block 1100.

At Block 1100, an intensity value of zero (0) is assigned to each pixel on the line linking the original key data point and the block point. This line is referred to as the blocking line and is illustrated in FIG. 10. Referring back to FIG. 8, corrected optical phase values for the pixels in and adjacent the local region are re-calculated based on the zero intensity values assigned to the pixels on the blocking line (Block 1200).

Figure 16A:
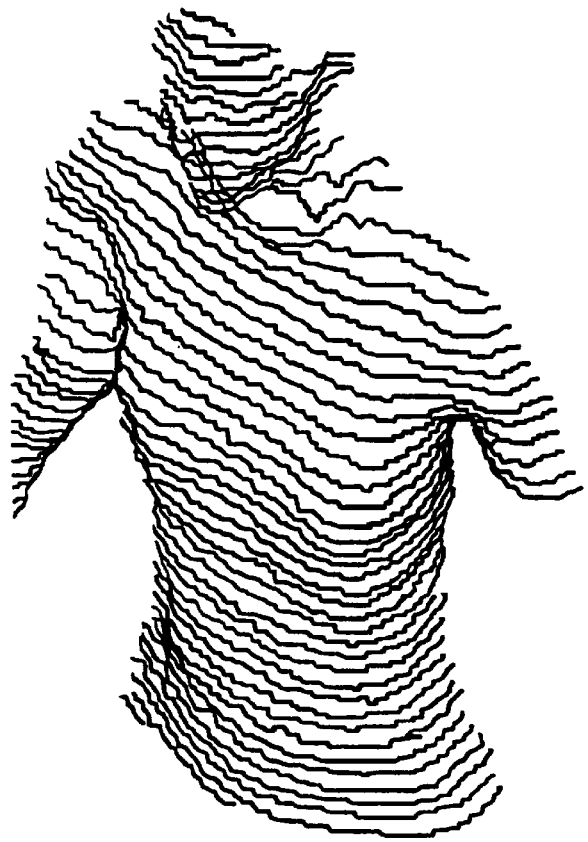
FIGS. 16A, 16B are illustrations of "xyz" data of the human body illustrated in FIGS. 4B, 4C with the jump order problem corrected.
Figure 16B:
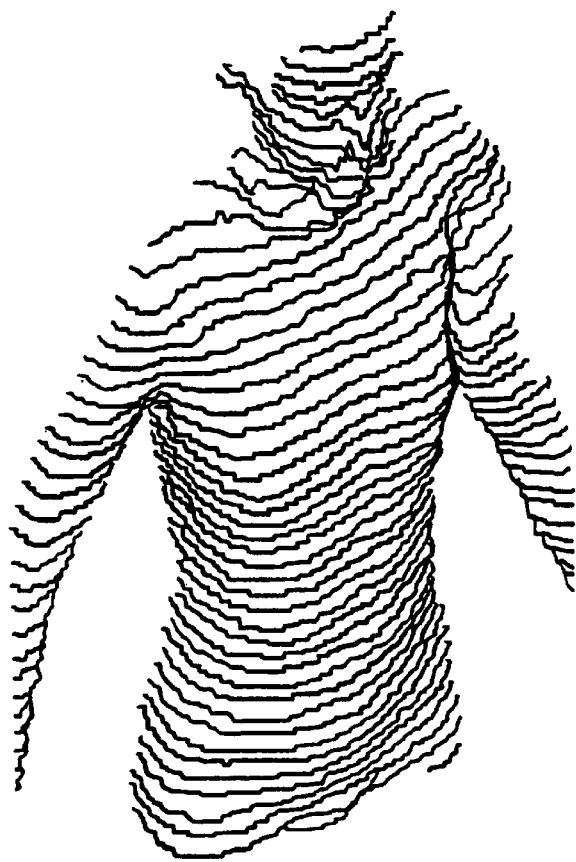

Finally, utilizing the corrected phase values, the surface contour for regions adjacent the apparent discontinuity illustrated in FIGS. 7 and 10 is re-calculated (Block 1300). As illustrated in FIGS. 16A and 16B, the surface contour of arms 32*a*, 32*b* can now be accurately measured using PMP techniques because correct phase orders are available for the arms and areas adjacent the region of overlap by the torso 30.

The present invention may be utilized in a variety of applications where it is desirable to accurately measure the contour of complex 3-D objects. A particularly well-suited application for the present invention is in conjunction with a body measurement system for the clothing industry. Heretofore, it was difficult to obtain an accurate measurement of the entire human body using PMP techniques, because of surface discontinuities resulting from overlapping portions of the body. Utilizing the present invention, an accurate mapping of the contour of the human body is possible.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A method for determining optical phase orders of pixels in a computer-generated image, wherein said image represents an object with a surface discontinuity therein and having a light beam with sinusoidally varying intensity projected thereon, said method comprising the steps of:

identifying a pixel as a key data point;

selecting a local region of the image surrounding a portion of the discontinuity and adjacent said key data point, wherein the local region comprises a sub-array of pixels;

identifying block points within the local region by performing the following steps for each of the pixels within the local region:

determining whether the value of the optical phase order of a first pixel minus the value of the optical phase order of an adjacent second pixel on the same row and previous column of the sub-array as the first pixel is less than zero;

determining whether the value of the optical phase order of the first pixel minus the value of the optical phase order of the adjacent second pixel on the same row and previous column of the sub-array as the first pixel is greater than one;

determining whether the value of the optical phase order of the first pixel minus the value of the optical phase order of the adjacent second pixel on the same row and previous column of the sub-array as the first pixel is equal to one, and determining whether the value of the optical phase order of a third pixel adjacent the first pixel on the same row and next column of the sub-array as the first pixel minus the value of the optical phase order of the first pixel is equal to one; and determining whether the absolute value of the optical phase order of the first pixel minus the optical phase order of a fourth pixel adjacent the first pixel on the same column of the sub-array as the first pixel is equal to one, and determining whether the absolute value of the optical phase order of the second pixel, adjacent the first pixel on the same row and previous column of the sub-array as the first pixel, minus the optical phase order of a fifth pixel, adjacent the second pixel on the same column of the sub-array as the second pixel and adjacent the fourth pixel on the same row of the sub-array as the fourth pixel, is equal to one;

linking the key data point and the identified block points with a blocking line;

assigning an intensity value of zero to each pixel located on the blocking line; and determining the optical phase order for pixels in the local region.

2. A method according to claim 1, wherein said step of identifying a pixel as a key data point comprises locating the pixel where the surface discontinuity begins.

3. A method according to claim 1, further comprising the step of determining whether the absolute value of the difference in intensity between a pair of adjacent pixels is greater than a threshold value, wherein each one of the pixels has a local maximum or minimum intensity value on the row, and wherein each one of the adjacent pixels is located on adjacent rows of the sub-array.

4. A method according to claim 3, wherein the threshold intensity value is about 50 grade value.

5. A method according to claim 3, further comprising the steps of:
   shifting the image by a single pixel in at least one direction; and
   subtracting from the image the row or column of pixels containing the pixel from which the image was shifted.

6. A method for determining, in a computing environment, the surface contour of an object having a surface discontinuity, said computing environment including a detector for receiving an image of the object, a display for displaying, via an array of pixels, the image of the object, and storage means for storing optical phase and intensity values for each pixel in the array, said method comprising the steps of:
   projecting a beam of light having a sinusoidally varying intensity pattern onto an object;
   receiving and storing a deformed grating image of the object for a plurality of phase shifts of said beam of light;
   determining, for points on the surface of the object represented by a pixel, the height at each point with respect to a reference plane;
   identifying a pixel as a key data point;
   selecting a local region of the received image of the object comprising a sub-array of pixels surrounding a portion of the discontinuity and adjacent said key data point;
   identifying block points within the local region by performing the following steps for each one of the pixels comprising the local region:
      determining whether the value of the optical phase order of a first pixel minus the value of the optical phase order of an adjacent second pixel on the same row and previous column of the sub-array as the first pixel is less than zero;
      determining whether the value of the optical phase order of the first pixel minus the value of the optical phase order of the adjacent second pixel on the same row and previous column of the sub-array as the first pixel is greater than one;
      determining whether the value of the optical phase order of the first pixel minus the value of the optical phase order of the adjacent second pixel on the same row and previous column of the sub-array as the first pixel is equal to one, and determining whether the value of the optical phase order of a third pixel adjacent the first pixel on the same row and next column of the sub-array as the first pixel minus the value of the optical phase order of the first pixel is equal to one; and
      determining whether the absolute value of the optical phase order of the first pixel minus the optical phase order of a fourth pixel adjacent the first pixel on the same column of the sub-array as the first pixel is equal to one, and determining whether the absolute value of the optical chase order of the second pixel, adjacent the first pixel on the same row and previous column of the sub-array as the first pixel, minus the optical phase order of a fifth pixel, adjacent the second pixel on the same column of the sub-array as the second pixel and adjacent the fourth pixel on the same row of the sub-array as the fourth pixel, is equal to one;
   linking the key data point and the identified block points with a blocking line;
   assigning an intensity value of zero to each pixel located on the blocking line;
   determining the optical phase order for each pixel in the local region; and
   utilizing determined optical phase orders for each pixel in the local region to determine, for points on the surface of the object adjacent the discontinuity represented by a pixel, the height at each point with respect to a reference plane.

7. A method according to claim 6 further comprising the step of determining whether the absolute value of the difference in intensity between a pair of adjacent pixels is greater than a threshold value, wherein each one of the pixels has a local maximum or minimum intensity value on the row, and wherein each one of the adjacent pixels is located on adjacent rows of the sub-array.

8. A method according to claim 7, wherein the threshold intensity value is about 50 grade value.

9. A method according to claim 7 further comprising the step of determining block points via edge detection methods.

10. A method for identifying block points on a computer-generated image of an object with a pattern of light projected thereon, said image comprising an array of pixels, said pattern of light having a sinusoidally varying intensity, said method comprising the steps of:
   locating each pair of adjacent pixels wherein each one of the pixels has a local maximum or minimum intensity value on the row;
   comparing the absolute value of the difference in intensity value of each one of the pair of adjacent pixels with a threshold intensity value;
   determining whether the value of the optical phase order of a first pixel minus the value of the optical phase order of an adjacent second pixel on the same row and previous column as the first pixel is less than zero;
   determining whether the value of the optical phase order of the first pixel minus the value of the optical phase order of the adjacent second pixel on the same row and previous column as the first pixel is greater than one;
   determining whether the value of the optical phase order of the first pixel minus the value of the optical phase order of the adjacent second pixel on the same row and previous column of the array as the first pixel is equal to one, and determining whether the value of the optical phase order of a third pixel adjacent the first pixel on the same row and next column as the first pixel minus the value of the optical phase order of the first pixel is equal to one; and
   determining whether the absolute value of the optical phase order of the first pixel minus the optical phase order of a fourth pixel adjacent the first pixel on the same column of the array as the first pixel is equal to one, and determining whether the absolute value of the optical phase order of the second pixel adjacent the first pixel on the same row and previous column of the array as the first pixel minus the optical phase order of a fifth pixel adjacent the second pixel on the same column as the second pixel and adjacent the fourth pixel on the same row of the array as the fourth pixel is equal to one.

11. A method according to claim 10, wherein the threshold intensity value is about 50 grade value.

12. A method according to claim 10 further comprising the steps of:

shifting the image by a single pixel in at least one direction; and subtracting from the image the row or column of pixels containing the pixel from which the image was shifted.

13. A system for determining the surface contour of an object having a surface discontinuity thereon, comprising:

means for projecting a beam of light having a sinusoidally varying intensity pattern onto an object;

means for receiving and storing a deformed grating image of the object for a plurality of phase shifts of said beam of light, said image comprising an array of pixels;

means for determining, for points on the surface of the object represented by a pixel, the height at each point with respect to a reference plane;

means for identifying a pixel as a key data point;

means for selecting a local region of the received image comprising a sub-array of pixels surrounding a portion of the discontinuity and adjacent said key data point;

means for identifying pixels within the sub-array as block points, comprising:

means for determining whether the value of the optical phase order of a first pixel minus the value of the optical phase order of an adjacent second pixel on the same row and previous column of the sub-array as the first pixel is less than zero;

means for determining whether the value of the optical phase order of the first pixel minus the value of the optical phase order of the adjacent second pixel on the same row and previous column of the sub-array as the first pixel is greater than one;

means for determining whether the value of the optical phase order of the first pixel minus the value of the optical phase order of the adjacent second pixel on the same row and previous column of the sub-array as the first pixel is equal to one, and determining whether the value of the optical phase order of a third pixel adjacent the first pixel on the same row and next column of the sub-array as the first pixel minus the value of the optical phase order of the first pixel is equal to one; and means for determining whether the absolute value of the optical phase order of the first pixel minus the optical phase order of a fourth pixel adjacent the first pixel on the same column of the sub-array as the first pixel is equal to one, and determining whether the absolute value of the optical phase order of the second pixel, adjacent the first pixel on the same row and previous column of the sub-array as the first pixel, minus the optical phase order of a fifth pixel, adjacent the second pixel on the same column of the sub-array as the second pixel and adjacent the fourth pixel on the same row of the sub-array as the fourth pixel, is equal to one;

means for linking the key data point and the block points with a blocking line;

means for assigning an intensity value of zero to each pixel located on the blocking line;

means for determining the optical phase order for each pixel in the sub-array; and means for utilizing determined optical phase orders for each pixel in the local region to determine, for points on the surface of the object adjacent the discontinuity represented by a pixel, the height at each point with respect to the reference plane.

14. A system according to claim 13 further comprising means for determining whether the absolute value of the difference in intensity between a pair of adjacent pixels is greater than a threshold value, wherein each one of the pixels has a local maximum or minimum intensity value on the row, and wherein each one of the adjacent pixels is located on adjacent rows of the sub-array.

15. A system according to claim 14 further comprising means for determining block points via edge detection methods.

16. A computer program product comprising:

a computer usable medium having computer readable program code means embodied in said medium for identifying block points on an image of an object having a pattern of light projected thereon, said image comprising an array of pixels;

computer readable program code means for locating each pair of adjacent pixels wherein each one of the pixels has a local maximum or minimum intensity value on the row;

computer readable program code means for comparing the absolute value of the difference in intensity value of each one of the pair of adjacent pixels with a threshold intensity value;

computer readable program code means for determining whether the value of the optical phase order of a first pixel minus the value of the optical phase order of an adjacent second pixel on the same row and previous column as the first pixel is less than zero;

computer readable program code means for determining whether the value of the optical phase order of the first pixel minus the value of the optical phase order of the adjacent second pixel on the same row and previous column as the first pixel is greater than one;

computer readable program code means for determining whether the value of the optical phase order of the first pixel minus the value of the optical phase order of the adjacent second pixel on the same row and previous column of the array as the first pixel is equal to one, and determining whether the value of the optical phase order of a third pixel adjacent the first pixel on the same row and next column as the first pixel minus the value of the optical phase order of the first pixel is equal to one; and computer readable program code means for determining whether the absolute value of the optical phase order of the first pixel minus the optical phase order of a fourth pixel adjacent the first pixel on the same column of the array as the first pixel is equal to one, and determining whether the absolute value of the optical phase order of the second pixel adjacent the first pixel on the same row and previous column of the array as the first pixel minus the optical phase order of a fifth pixel adjacent the second pixel on the same column as the second pixel and adjacent the fourth pixel on the same row of the array as the fourth pixel is equal to one.

17. A computer program product according to claim 16 further comprising computer readable program code means for determining block points via edge detection methods.

* * * * *

UNITED STATES PATENT AND TRADEMARK OFFICE
CERTIFICATE OF CORRECTION

PATENT NO. : 5,953,448
DATED : September 14, 1999
INVENTOR(S) : Liang

It is certified that error appears in the above-identified patent and that said Letters Patent is hereby corrected as shown below:

In the Claims

Column 15, line 65, delete "chase" and insert - - phase - -.

Signed and Sealed this

Thirteenth Day of June, 2000

Attest:

Q. TODD DICKINSON

*Attesting Officer*    *Director of Patents and Trademarks*